(12) United States Patent
Scifert et al.

(10) Patent No.: US 11,369,474 B2
(45) Date of Patent: Jun. 28, 2022

(54) BONE IMPLANT HAVING A MESH

(71) Applicant: Warsaw Orthopedic, Inc., Warsaw, IN (US)

(72) Inventors: Jeffrey L. Scifert, Arlington, TN (US); Rodney R. Ballard, Lakeland, TN (US); Christopher M. Patterson, Olive Branch, MS (US); Scott M. Vickers, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/651,855

(22) Filed: Jul. 17, 2017

(65) Prior Publication Data

US 2019/0015209 A1 Jan. 17, 2019

(51) Int. Cl.
*A61B 17/70* (2006.01)
*A61F 2/28* (2006.01)
(Continued)

(52) U.S. Cl.
CPC ........ *A61F 2/2846* (2013.01); *A61B 17/7002* (2013.01); *A61B 17/7074* (2013.01); *A61F 2/28* (2013.01); *A61F 2/30749* (2013.01); *A61F 2/4601* (2013.01); *A61B 17/3468* (2013.01); *A61F 2002/2835* (2013.01)

(58) Field of Classification Search
CPC .... A61F 2/2846; A61F 2/30749; A61F 2/285; A61F 2/30751–30752; A61B 17/3468
See application file for complete search history.

(56) References Cited

U.S. PATENT DOCUMENTS 5,503,164 A * 4/1996 Friedman ........... A61B 17/8085
128/897
5,545,178 A * 8/1996 Kensey .............. A61B 17/0057
604/15

(Continued)

FOREIGN PATENT DOCUMENTS

WO 2012116319 A1 8/2012

OTHER PUBLICATIONS

Extended European Search Report dated Mar. 21, 2019, issued by the European Patent Office in EP Application No. 18181628.1 for Bone Implant Having a Mesh filed on Jul. 4, 2018.

(Continued)

*Primary Examiner* — Eduardo C Robert
*Assistant Examiner* — Steven J Cotroneo
(74) *Attorney, Agent, or Firm* — Sorell, Lenna & Schmidt, LLP; William D. Schmidt, Esq.

(57) ABSTRACT

A kit for deploying a bone implant at a surgical site is provided. The kit comprises a first sleeve having an interior surface that defines a channel, and a second sleeve having an outer surface and an inner surface. The inner surface of the second sleeve defines an inner channel. The outer surface of the second sleeve is configured to slidably engage the interior surface of the channel of the first sleeve. A bone implant is also provided comprising a mesh material. The mesh material is disposed in a portion of the channel of the first sleeve or disposed in a portion of the inner channel of the second sleeve or disposed in both the portion of the channel of the first sleeve and the portion of the inner channel of the second sleeve.

6 Claims, 9 Drawing Sheets

(51) Int. Cl.
*A61F 2/46* (2006.01)
*A61F 2/30* (2006.01)
*A61B 17/34* (2006.01)

(56) References Cited

U.S. PATENT DOCUMENTS

| | | | |
|---|---|---|---|
| 5,713,921 A * | 2/1998 | Bonutti | A61B 17/0401 606/232 |
| 5,741,257 A * | 4/1998 | Kirsch | A61B 17/80 606/215 |
| 6,494,883 B1 | 12/2002 | Ferree | |
| 7,341,601 B2 * | 3/2008 | Eisermann | A61B 17/68 623/17.11 |
| 8,109,935 B2 * | 2/2012 | Stoffel | A61F 2/4601 606/99 |
| 8,197,550 B2 | 6/2012 | Brown et al. | |
| 8,241,298 B2 * | 8/2012 | Sengun | A61F 2/4618 606/108 |
| 8,454,666 B2 | 6/2013 | Tornier | |
| 8,663,296 B2 | 3/2014 | Williams | |
| 8,808,329 B2 * | 8/2014 | Bonutti | A61B 17/0401 606/232 |
| 9,101,475 B2 | 8/2015 | Wei et al. | |
| 9,168,151 B2 | 10/2015 | Sweeney et al. | |
| 9,198,758 B2 | 12/2015 | McKay | |
| 9,220,598 B2 | 12/2015 | Betz et al. | |
| 9,241,797 B2 | 1/2016 | McKay | |
| 9,271,766 B2 | 3/2016 | Bonutti | |
| 9,333,082 B2 | 5/2016 | Wei et al. | |
| 9,433,707 B2 | 9/2016 | Swords et al. | |
| 9,492,278 B2 | 11/2016 | Wei et al. | |
| 9,504,467 B2 | 11/2016 | Ostrovsky et al. | |
| 2002/0173806 A1 * | 11/2002 | Giannetti | A61L 27/3629 606/151 |
| 2003/0236573 A1 * | 12/2003 | Evans | A61L 27/12 623/23.58 |
| 2005/0038520 A1 * | 2/2005 | Binette | A61L 27/38 623/18.11 |
| 2005/0043733 A1 | 2/2005 | Eisermann et al. | |
| 2005/0143826 A1 * | 6/2005 | Zucherman | A61F 2/442 623/17.16 |
| 2005/0216087 A1 * | 9/2005 | Zucherman | A61F 2/441 623/17.16 |
| 2005/0256582 A1 * | 11/2005 | Ferree | A61B 17/7059 623/17.16 |
| 2005/0267555 A1 * | 12/2005 | Marnfeldt | A61B 90/30 607/116 |
| 2006/0247665 A1 * | 11/2006 | Ferree | A61B 17/1671 606/151 |
| 2009/0132047 A1 * | 5/2009 | Mansmann | A61F 2/0811 623/14.12 |
| 2009/0182427 A1 | 7/2009 | Liu et al. | |
| 2009/0317447 A1 * | 12/2009 | Hsiao | A61F 2/28 424/426 |
| 2010/0076503 A1 | 3/2010 | Beyar et al. | |
| 2011/0054408 A1 | 3/2011 | Wei et al. | |
| 2013/0158610 A1 | 6/2013 | Hernandez | |
| 2013/0261634 A1 | 10/2013 | McKay | |
| 2014/0031795 A1 | 1/2014 | McKay | |
| 2014/0147814 A1 | 5/2014 | Collins et al. | |
| 2014/0212471 A1 | 7/2014 | Drapeau et al. | |
| 2016/0038207 A1 | 2/2016 | Wei et al. | |
| 2016/0106482 A1 | 4/2016 | Rains | |
| 2016/0250038 A1 | 9/2016 | Wei et al. | |
| 2016/0318247 A1 | 11/2016 | Schlachter | |

OTHER PUBLICATIONS

Japanese Office Action dated Dec. 3, 2021 issued by the Japan Patent Office in corresponding Japanese Application No. 2018-132150 for Bone Implant Having a Mesh (translation provided).

Chinese Office Action dated Sep. 3, 2021 issued by the Chinese State IP Office in corresponding Chinese Application No. 201810775529.9 for Bone Implant Having a Mesh (translation provided).

* cited by examiner

BONE IMPLANT HAVING A MESH

BACKGROUND

The use of bone grafts and bone substitute materials in orthopedic medicine is known. While bone wounds can regenerate without the formation of scar tissue, fractures and other orthopedic injuries take a long time to heal, during which time the bone is unable to support physiologic loading unaided. Metal pins, screws, rods, plates and meshes are frequently required to replace the mechanical functions of injured bone. However, metal is significantly more stiff than bone. Use of metal implants may result in decreased bone density around the implant site due to stress shielding. Physiologic stresses and corrosion may cause metal implants to fracture. Unlike bone, which can heal small damage cracks through remodeling to prevent more extensive damage and failure, damaged metal implants can only be replaced or removed. The natural cellular healing and remodeling mechanisms of the body coordinate removal of bone and bone grafts by osteoclast cells and formation of bone by osteoblast cells.

Conventionally, bone tissue regeneration is achieved by filling a bone repair site with a bone graft. Over time, the bone graft is incorporated by the host and new bone remodels the bone graft. In order to place the bone graft, it is common to use a monolithic bone graft or to form an osteoimplant comprising particulated bone in a carrier. Generally, the formed implant, whether monolithic or particulated and in a carrier is substantially solid at the time of implantation and thus does not conform to the implant site. The implant is also substantially complete at the time of implantation and thus provides little ability for customization, for example by the addition of autograft.

Further, formed implants oftentimes migrate away from the bone repair site due to their shape and solid state. In order to ensure a good outcome for graft fusion, it is often beneficial to ensure that the bone graft does not migrate from the repair site. It is also beneficial to implement methods and devices that facilitate proper graft fixation and placement.

The use of bone grafts is generally limited by the available shape and size of grafts. Bone grafts using cortical bone remodel slowly because of their limited porosity. Traditional bone substitute materials and bone chips are more quickly remodeled but cannot immediately provide mechanical support. In addition, while bone substitute materials and bone chips can be used to fill oddly shaped bone defects, such materials are not as well suited for wrapping or resurfacing bone.

Therefore, it would be beneficial to provide customizable bone implants, devices and kits that reduce or prevent graft migration at a surgical site. Methods of implanting these customizable bone implants and devices would also be beneficial.

SUMMARY

Improved bone implants, devices, kits and methods are provided that reduce or prevent migration of bone implants after they are deployed to a surgical site. In one embodiment, a kit for deploying a bone implant at a surgical site is provided. The kit comprises a first sleeve (e.g., a first dilator) having an interior surface that defines a channel. A second sleeve (e.g., a second dilator) is provided having an outer surface and an inner surface. The inner surface of the second sleeve defines an inner channel. The outer surface of the second sleeve is configured to slidably engage the interior surface of the channel of the first sleeve. A bone implant is also provided comprising a mesh material. The mesh material is disposed in a portion of the channel of the first sleeve or disposed in a portion of the inner channel of the second sleeve or disposed in both the portion of the channel of the first sleeve and the portion of the inner channel of the second sleeve, such that sliding the outer surface of the second sleeve deploys the bone implant at the surgical site.

In some embodiments, a bone implant is provided. The bone implant comprises a mesh body having a distal end and a proximal end, and a compartment disposed therebetween. The compartment is configured to receive a bone material. A first cylindrical member is provided that is disposed at or near the proximal end of the mesh body and a second cylindrical member is provided that is disposed at or near the distal end of the mesh body. The first and second cylindrical members are configured for engagement with a spinal rod to facilitate containment of the bone material at a surgical site.

The first and second cylindrical members comprise a through hole configured to receive a screw to secure the mesh material or the first and second cylindrical members on the spinal rod. The first and second cylindrical members are resorbable grommets that are configured for at least slidable engagement with the spinal rod. In some embodiments, the mesh material is net shaped, hammock shaped, a bag, is a rigid cannulated preformed shape, or a combination thereof. The bone material comprises fully demineralized bone fibers and surface demineralized bone chips.

In one embodiment, a bone implant is provided. The bone implant comprises a bone material body comprising a proximal end and a distal end. The proximal end comprises a head portion having a first opening configured to receive a bone fastener. The bone implant also includes a bone material covering configured to at least partially enclose the bone material body. The bone material covering includes a proximal end and a distal end and a channel disposed therebetween. The channel is configured to slidably receive the proximal end and the distal end of the bone material body. The bone material covering includes a second opening intersecting with and transverse to the channel. The second opening is configured to align with the first opening and receive a bone fastener when the bone material body is slidably received in the channel of the bone material covering.

In some embodiments, the bone material covering comprises a third opening to facilitate release of the bone material. In some embodiments, the bone material body comprises an elongated portion and the bone material covering comprises an elongated covering portion. The elongated portion of the bone material body corresponds to the elongated covering portion of the bone material covering such that the bone material body is completely enclosed by the bone material covering.

In some embodiments, a method of implanting a bone implant at a surgical site beneath the skin of a patient is provided, the method comprising: delivering to the surgical site a plurality of bone fasteners, a spinal rod, and the bone implant, the bone implant comprising a mesh body having a distal end and a proximal end and a compartment disposed therebetween, the compartment configured to receive a bone material, a first cylindrical member disposed at or near the proximal end of the mesh body, the first cylindrical member configured for engagement with the spinal rod to facilitate containment of the bone material at the surgical site, and a second cylindrical member disposed at or near the distal end of the mesh body, the second cylindrical member configured for engagement with the spinal rod to facilitate containment of the bone material at the surgical site; attaching the plurality of bone fasteners to surgical site; attaching the first and second cylindrical members to the spinal rod; and attaching the spinal rod to the plurality of bone fasteners in a fixed engagement.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

The present disclosure will become more readily apparent from the specific description accompanied by the following drawings, in which:

In FIG. 1, the bone implant is disposed in a portion of an inner channel of the second sleeve such that sliding an outer surface of the second sleeve deploys the bone implant at the surgical site.

In FIG. 2, the bone implant is disposed in both a portion of the channel of the first sleeve and a portion of the inner channel of the second sleeve, such that sliding the outer surface of the second sleeve deploys the bone implant at the surgical site.

Figure 1:
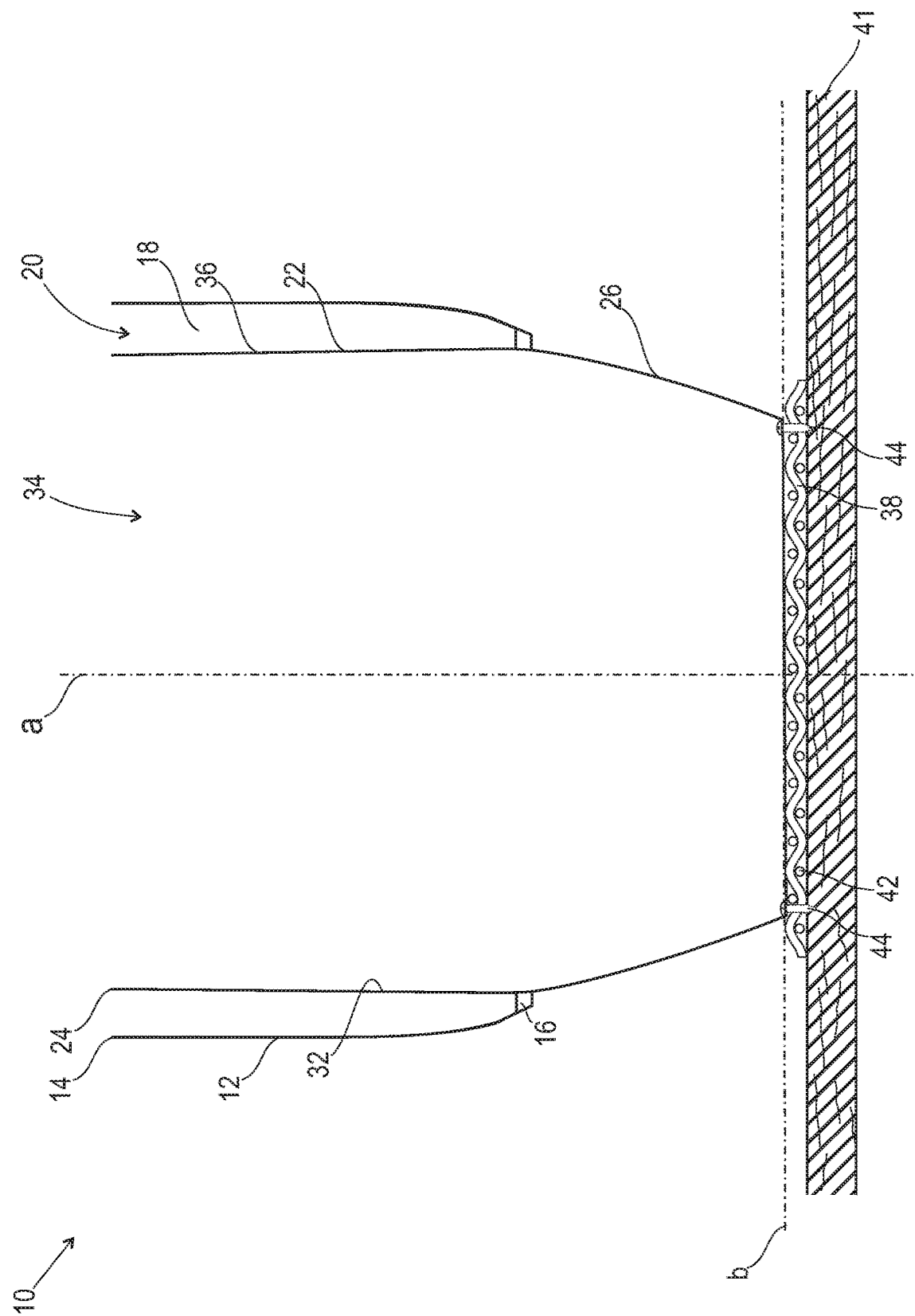
FIG. 1 is a cross sectional view of a kit for deploying a bone implant to a surgical site. The kit comprises a first sleeve (e.g., dilator) and a second sleeve (e.g., dilator). The second sleeve is configured for slidable engagement with a channel of the first sleeve. A bone implant is also provided comprising a mesh material. The first sleeve and the second sleeve deploy the bone implant into the surgical site. The bone implant is then attached to the surgical site via fastening elements.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, for example, 5.5 to 10.

Bioactive agent or bioactive compound is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, antidepressants, anti-psychotic substances, anti-emetics, and imaging agents. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present application may be found in Pharmaceutical Substances: Syntheses, Patents, Applications by Axel Kleemann and Jurgen Engel, Thieme Medical Publishing, 1999; Merck Index: An Encyclopedia of Chemicals, Drugs, and Biologicals, edited by Susan Budavari et al., CRC Press, 1996; and United States Pharmacopeia-25/National Formulary-20, published by the United States Pharmacopeia Convention, Inc., Rockville Md., 2001, each of which is incorporated herein by reference.

Biocompatible, as used herein, is intended to describe materials that, upon administration in vivo, do not induce undesirable long-term effects.

Bone, as used herein, refers to bone that is cortical, cancellous or cortico-cancellous of autogenous, allogenic, xenogenic, or transgenic origin.

Bone graft, as used herein, refers to any implant prepared in accordance with the embodiments described herein and therefore may include expressions such as bone material and bone membrane.

Demineralized, as used herein, refers to any material generated by removing mineral material from tissue, for example, bone tissue. In certain embodiments, demineralized bone material may be added to the bone void filler. The demineralized bone material described herein include preparations containing less than 5%, 4%, 3%, 2% or 1% calcium by weight. Partially demineralized bone (for example, preparations with greater than 5% calcium by weight but containing less than 100% of the original starting amount of calcium) is also considered within the scope of the disclosure. In some embodiments, partially demineralized bone contains preparations with greater than 5%, 10%⁰, 150%, 20%, 25%, 30%, 35%, 40%, 45%, 50%, 55%, 60%, 65%, 70%, 75%, 80%, 85%, 900/%, 95%, 96%, 97%, 98% or 99% of the original starting amount of calcium. In some embodiments, demineralized bone has less than 95% of its original mineral content. In some embodiments, demineralized bone has less than 95%, 900/%, 85%, 80° %, 75%, 70%, 65%, 60%, 55%, 50%, 45%, 40%, 35%, 30%, 25%, 20%, 15%, 10%, or 5% of its original mineral content. Demineralized is intended to encompass such expressions as "substantially demineralized," "partially demineralized," "superficially demineralized," and "fully demineralized." In some embodiments, part or all of the surface of the bone can be demineralized. For example, part or all of the surface of the bone material can be demineralized to a depth of from about 100 to about 5000 microns, or about 150 microns to about 1000 microns. In some embodiments, part or all of the surface of the bone material can be demineralized to a depth of from about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950 to about 5000 microns. If desired, the bone material can comprise demineralized material.

Partially demineralized bone is intended to refer to preparations with greater than 5% calcium by weight but containing less than 100% of the original starting amount of calcium. In some embodiments, partially demineralized bone comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In some embodiments, the DBM compositions include preparations that contain less than 5, 4, 3, 2 and/or 1% calcium by weight. In other embodiments, the DBM compositions comprise partially demineralized bone (for example, preparations with greater than 5% calcium by weight but containing less than 100°/% of the original starting amount of calcium).

Osteoconductive, as used herein, refers to the ability of a substance to serve as a template or substance along which bone may grow.

Osteogenic, as used herein, refers to materials containing living cells capable of differentiation into bone tissue.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

Superficially demineralized, as used herein, refers to bone-derived elements possessing at least about 90 weight percent of their original inorganic mineral content. In some embodiments, superficially demineralized contains at least about 90, 91, 92, 93, 94, 95, 96, 97, 98 and/or 99 weight percent of their original inorganic material. The expression "fully demineralized" as used herein refers to bone containing less than 8% of its original mineral context. In some embodiments, fully demineralized contains about less than 8, 7, 6, 5, 4, 3, 2 and/or 1% of its original mineral content.

The expression "average length to average thickness ratio" as applied to the DBM fibers of the present application means the ratio of the longest average dimension of the fiber (average length) to its shortest average dimension (average thickness). This is also referred to as the "aspect ratio" of the fiber.

Fibrous, as used herein, refers to bone elements whose average length to average thickness ratio or aspect ratio of the fiber is from about 50:1 to about 1000:1. In some embodiments, average length to average thickness ratio or aspect ratio of the fiber is from about 50:1, 75:1, 100:1, 125:1, 150:1, 175:1, 200:1, 225:1, 250:1, 275:1, 300:1, 325:1, 350:1, 375:1, 400:1, 425:1, 450:1, 475:1, 500:1, 525:1, 550:1, 575:1, 600:1, 625:1, 650:1, 675:1, 700:1, 725:1, 750:1, 775:1, 800:1, 825:1, 850:1, 875:1, 900:1, 925:1, 950:1, 975:1 and/or 1000:1. In overall appearance, the fibrous bone elements can be described as bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the bone fibers are of irregular shapes including, for example, linear, serpentine or curved shapes. The bone fibers are demineralized, however some of the original mineral content may be retained when desirable for a particular embodiment. In various embodiments, the bone fibers are mineralized. In some embodiments, the fibers are a combination of demineralized and mineralized.

Non-fibrous, as used herein, refers to elements that have an average width substantially larger than the average thickness of the fibrous bone element or aspect ratio of less than from about 50:1 to about 1000:1. The non-fibrous bone elements are shaped in a substantially regular manner or specific configuration, for example, triangular prism, sphere, cube, cylinder and other regular shapes. By contrast, particles such as chips, shards, or powders possess irregular or random geometries. It should be understood that some variation in dimension will occur in the production of the elements of this application and elements demonstrating such variability in dimension are within the scope of this application and are intended to be understood herein as being within the boundaries established by the expressions "mostly irregular" and "mostly regular."

The term "grommet" refers to a ring or edge strip. Grommets are generally flared or collared on each side to keep them in place. These may, in some embodiments, slidably engage a rod.

The term "bone fastener" or "bone fasteners" refer to multi-axial screws, uni-axial screws, fixed axis screws, sagittal adjusting screws, transverse sagittal adjusting screws, pedicle screws, uni-planar screws, facet screws, tissue penetrating screws, conventional screws, expanding screws and/or posts.

The bone implants, devices, kits and methods may be employed to treat spinal disorders such as, for example, degenerative disc disease, disc herniation, osteoporosis, spondylolisthesis, stenosis, scoliosis and other curvature abnormalities, kyphosis, tumor and fractures. The bone implants, devices, kits and methods may be employed with other osteal and bone related applications, including those associated with diagnostics and therapeutics. They may also be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The bone implants, devices, kits and methods may also be alternatively employed with procedures for treating the lumbar, cervical, thoracic, sacral and pelvic regions of a spinal column. They may also be used on animals, bone models and other non-living substrates, such as, for example, in training, testing and demonstration.

In various embodiments, the bone implant comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

In some embodiments, the bone implants, devices, kits and methods are used in minimally invasive surgeries to provide for optimized workflow when creating or decorticating posterior-fusion beds and to deliver bone graft.

In one embodiment, a built-in internal slide mechanism which mates to an inner diameter of a sequential dilator is provided. A resorbable bone net mesh is attached to the mechanism such that the mechanism can place the bone net mesh through the dilator to overlay a fusion site and bone graft that is placed in the fusion site. The bone net mesh is then anchored to the fusion site via resorbable tacks or screws to localize the bone graft at the fusion site and to prevent migration. The bone graft can also be placed into the bone net mesh itself and then lowered to the fusion site where it is then localized inside the bone net mesh when tacked in place.

In one embodiment, a bone net mesh is provided that can be designed with an attachment mechanism, such as, for example built-in resorbable grommets. The attachment mechanisms are configured to affix the bone net mesh to pedicle screw rods, allowing for placement of the bone net mesh at the fusion site.

In one embodiment, screws are designed with offsets to allow for fixation of the bone net mesh at the fusion site in order to maintain graft placement. Alternatively, the offsets are designed to hold the grafts in place.

In some embodiments, the embodiments described above are provided in a single embodiment and provide a simple to use, an all-in-one system which can be used with existing spinal fixation instruments. The system provides graft delivery and graft localization capability to minimally invasive surgery and mini-open procedures for boney fusion. The system can be used to work with existing bone grafting options such as Magnifuse®, available from Metronic, Inc. and other products.

Kit

Figure 2:
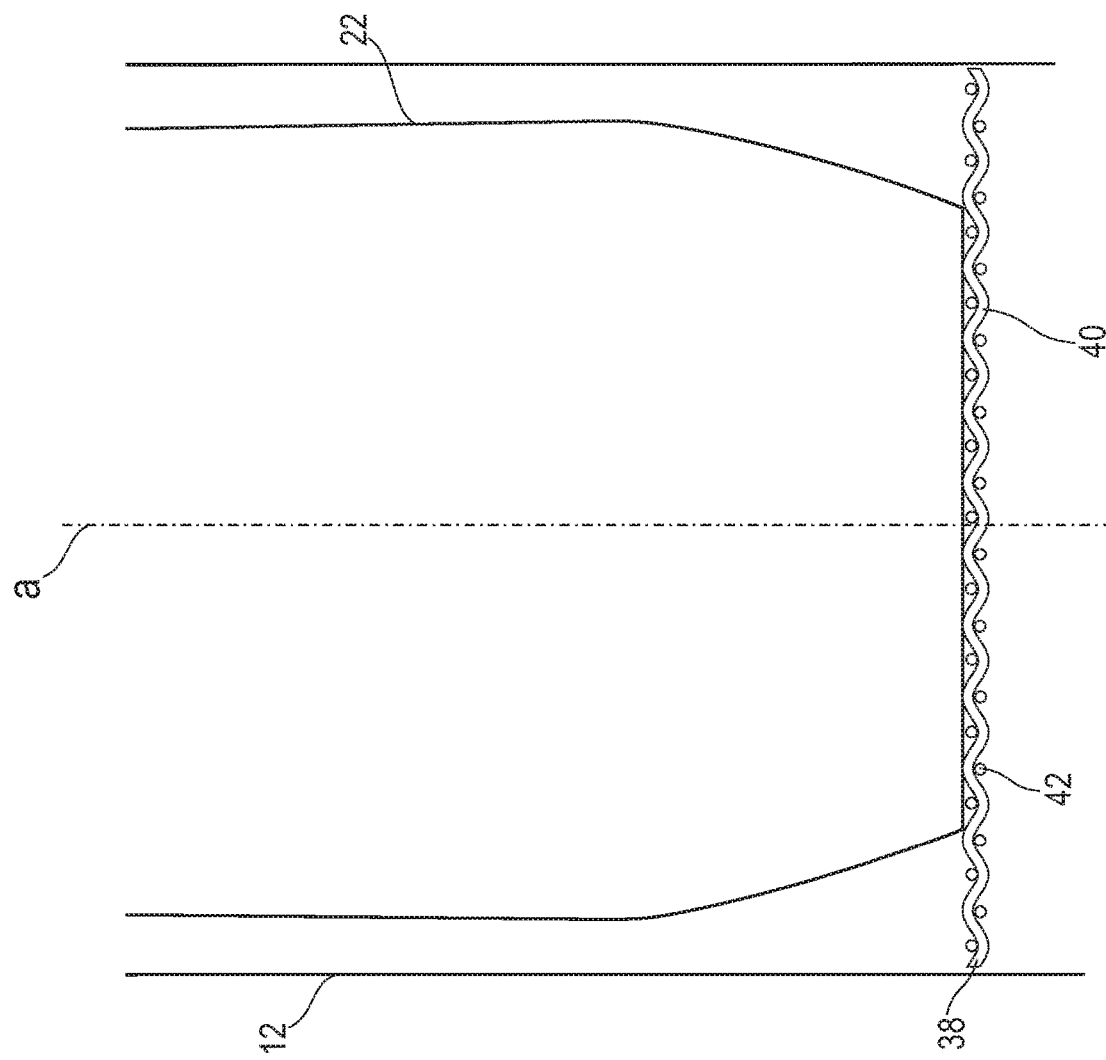
FIG. 2 is a cross sectional view of components of the kit of FIG. 1.
Figure 3:
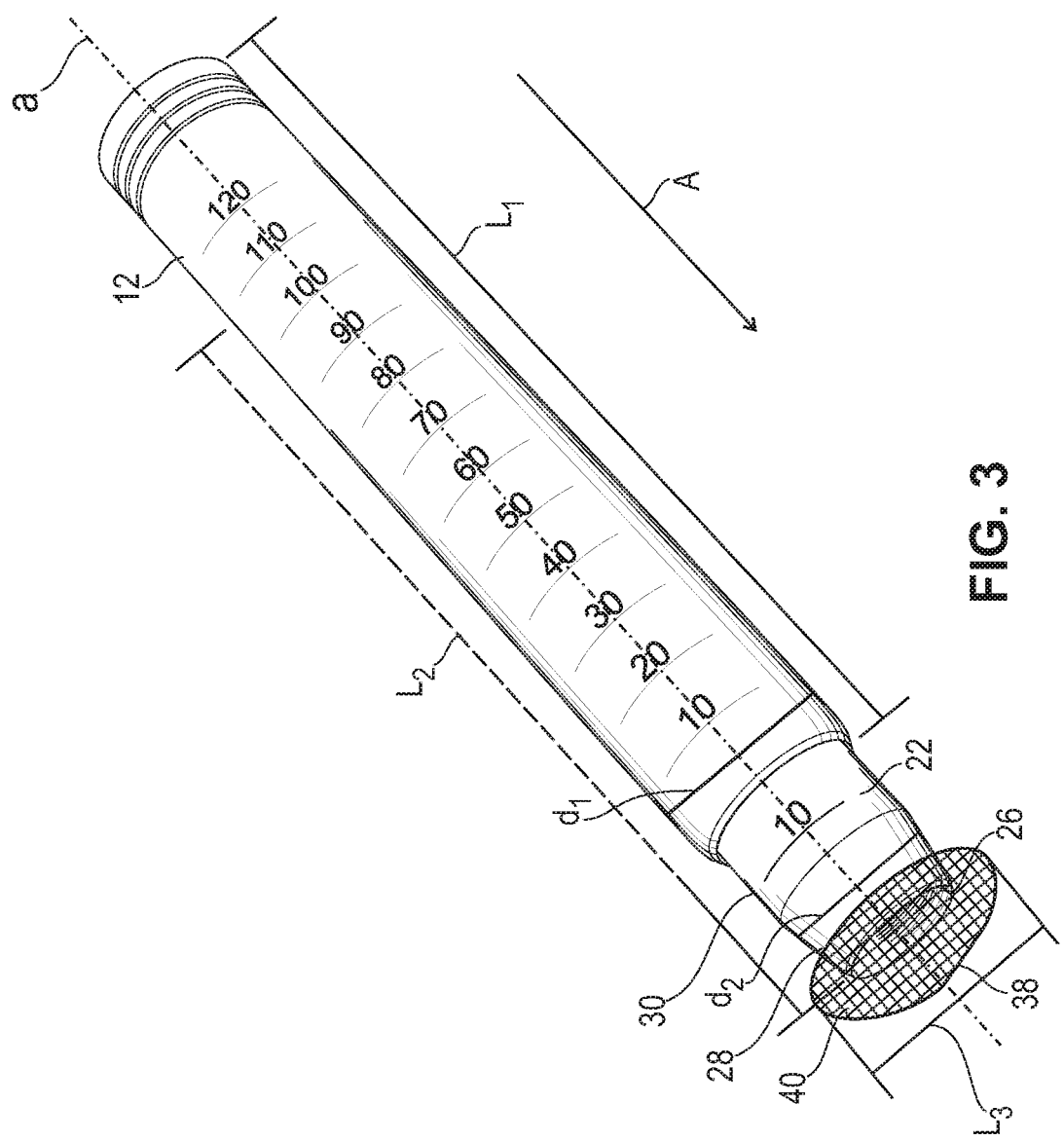
FIG. 3 is a perspective view of the second sleeve disposed within the channel of the first sleeve of FIG. 1, and the mesh material extends longitudinal out of the first and second sleeves.

Referring to FIGS. 1 to 3, a kit 10 is provided that is configured to deploy a bone implant to a surgical site 41 and prevent the bone implant from migrating from the surgical site after deployment. The kit comprises a first sleeve, such as, for example, a first dilator 12. The first dilator is configured for engagement with a second sleeve (e.g., a second dilator) and a bone implant such that the bone implant is deployed to a surgical site (e.g., fusion site). The first dilator includes a proximal end 14 and a distal end 16, and a longitudinal axis a that is disposed between the ends. The distal end may be a tapered shape depending on the location of the surgical site. The first dilator comprises an interior surface 18 that defines a channel 20 that is configured for slidable engagement with an outer surface and/or an engagement member of the second dilator. The channel may be smooth, textured or may mate with the engagement member.

The first dilator includes a diameter $d_1$ that is greater than a diameter of the second dilator. The diameter of the first dilator may be from about 12 millimeters (mm) to about 100 mm, from about 20 mm to about 80 mm, from about 25 mm to about 70 mm, from about 30 to about 60 mm, or from about 40 mm to about 50 mm. The first dilator may be a selected length $L_1$, such as, for example, from about 1 inch to about 20 inches, from about 1 inch to about 15 inches, from about 1 inch to about 10 inches, from about 1 inch to about 5 inches, from about 5 inches to about 20 inches, from about 5 inches to about 15 inches, from about 5 inches to about 10 inches, from about 10 inches to about 20 inches or from about 10 inches to about 15 inches. The first dilator may be color coded such that a medical practitioner may easily select the correct dilator diameter for a particular surgical site. The first dilator may also include visual indicia, such as, for example, gradations disposed on an outer surface that are configured to provide a visual indication of the progression of movement and depth of the dilator down a surgical pathway to the surgical site.

The kit also includes a second sleeve, such as, for example a second dilator 22. The second dilator is configured for slidable engagement with the channel of the first dilator and a bone implant, such that the bone implant can be deployed to a surgical site (e.g., fusion site). The second dilator comprises a proximal end 24 and a distal end 26, and longitudinal axis a is disposed between the ends. The distal end is configured for engagement with a portion of the bone implant. The distal end may include a capturing mechanism 28 that assists the second dilator in engaging with the bone implant. In some embodiments, the capturing mechanism may include, but is not limited to a chemical capturing mechanism such as a bioadhesive or glue, cement, tape, tissue adhesives, or a combination thereof. The capturing mechanism may also be a mechanical capturing mechanism such as hooks, anchors, buttons, clips, snaps, friction fittings, compressive fittings, expanding rivets, staples, nails, posts, connectors, or a combination thereof.

The second dilator includes an outer surface 30 and an inner surface 32 that defines an inner channel 34. The outer surface includes an engagement member 36 that is configured for slidable engagement with the channel of the first dilator. The engagement member may comprise teeth, grooves, a press-fit surface, a keyed surface, ball bearings, or a combination thereof. The engagement member can be made from one or more metals, plastics, polymers, or a combination thereof, as disclosed herein. The inner channel is configured for engagement with at least a portion of the bone implant.

In some embodiments, a portion of the bone implant is disposed in the channel of the first dilator, is disposed in a portion of the inner channel of the second dilator, or a portion of the implant is disposed in both the portion of the channel of the first dilator and the portion of the inner channel of the second dilator, as shown in FIG. 2, such that sliding the outer surface of the second dilator in a direction shown by arrow A in FIG. 3 deploys the bone implant at the surgical site. The second dilator includes a diameter $d_2$ that is less than the diameter $d_1$ of the first dilator. The diameter of second dilator may be from about 8 millimeters (mm) to about 80 mm, from about 10 mm to about 70 mm, from about 15 mm to about 60 mm, from about 20 to about 50 mm, or from about 30 mm to about 40 mm. The second dilator may be a selected length $L_2$, such as, for example, from about 1 inch to about 20 inches, from about 1 inch to about 15 inches, from about 1 inch to about 10 inches, from about 1 inch to about 5 inches, from about 5 inches to about 20 inches, from about 5 inches to about 15 inches, from about 5 inches to about 10 inches, from about 10 inches to about 20 inches or from about 10 inches to about 15 inches. The second dilator may be color coded such that a medical practitioner may easily select the correct second dilator diameter for a particular surgical site. The second dilator may also include visual indicia, such as, for example, gradations disposed on an outer surface that are configured to provide a visual indication of the progression of movement and depth of the second dilator down the channel of the first dilator and/or a surgical pathway to the surgical site.

For example, the surface area of the mesh material 40 may have a diameter and/or length greater than the diameter of the first dilator and/or the second dilator. In the compressed configuration shown in FIG. 2, the mesh material 40 is held within first dilator 12, as the diameter of the first dilator is small and the mesh is compressed within the dilator. However, when the mesh material 40 is deployed from the first dilator 12, the mesh material 40 expands to an uncompressed or expanded state as shown in FIG. 3 where it can enclose the bone material or be fastened to the surgical site. In this way, the bone material will not migrate from the surgical site. In some embodiments, the second dilator 22 can be used to position the mesh material 40 and/or bone material 42 at the surgical site 41.

The kit further includes a bone implant 38 comprising a mesh material 40 and a bone material 42. The bone implant is disposed on transverse axis b. The mesh material can be made from a resorbable natural or synthetic polymer including, but not limited to, at least one of poly(lactic acid) (PLA), poly(glycolic acid) (PGA), poly(lactic-co-glycolic acid) (PLGA), silk, or a combination thereof. The mesh material may include a selected weave pattern to impart flexibility and stretchable characteristics to the mesh. The mesh material can also be braided.

The mesh material may have varying degrees of permeability. It may be permeable, semi-permeable, or non-permeable. Permeability may be with respect to cells, to liquids, to proteins, to growth factors, to bone morphogenetic proteins, or other. In alternative embodiments, the mesh material may comprise a substantially solid structure, such as a polymer structure with a chamber, compartment or a spun cocoon.

The mesh material may have any suitable configuration. For example, the mesh material may be formed as a bag, a ring, a cylinder, a cage, a rectangular shape, a suture-like wrap, a continuous tube, or any other configuration. The mesh material may also comprise a single or a plurality of compartments. For example, in a tubular embodiment, the tube may be formed into a plurality of compartments by tying a cord around the tube at one or more points, or by other suitable mechanism such as crimping, twisting, knotting, stapling, sewing, or other. The configuration of the mesh material may be determined by the type of bone material to be provided within the mesh material.

The mesh material itself can be a porous mesh such that fluid transfer and cell infiltration can occur so that osteoblasts can manufacture bone graft. The porous mesh material can have a pore size of from about 1 micron to about 2000 microns, from about 1 micron to about 1500 microns, from about 1 micron to about 1000 microns, from about 1 micron to about 500 microns, from about 1 micron to about 250 microns, from about 100 micron to about 2000 microns, from about 150 to about 1500 microns, from about 200 to about 1000 microns, from about 250 to about 500 microns. In some embodiments, the pore size can be about 1, 10, 20, 50, 80, 100, 120, 150, 180, 200, 220, 250, 280, 300, 350, 400, 450, 500, 550, 600, 650, 700, 750, 800, 850, 900, 950, 1000, 1250, 1450, 1650, 1850, and/or 2000 microns.

The mesh material includes a length L3, and in some embodiments, length L3 is greater than diameter d2 of the second dilator but is smaller than diameter d1 of the first dilator. In some embodiments, length L3 is greater than both diameters d1 and d2, or is less than both diameters d1 and d2. The length of the mesh material may be from about 5 millimeters (mm) to about 120 mm, from about 10 millimeters to about 90 mm, from about 8 mm to about 80 mm, from about 20 mm to about 70 mm, from about 30 to about 60 mm, or from about 40 mm to about 50 mm.

The mesh material can also comprise a first layer and a second layer, with the bone material disposed therebetween. The first layer of mesh material can be deployed to the surgical site via the sliding engagement of the first and second dilators. A layer of bone material can then be deposited on top of the first layer of mesh material and then the second layer of mesh material can be deployed on top of the bone material. The first layer and second layer of mesh material are then fused together via Velcro®, an adhesive, clips, tacks, or tape that was either already applied to the mesh before deployment to the surgical site or is applied to the mesh after deployment to the surgical site. The mesh material can also be custom made before deployment to the surgical site or the mesh material can be prefilled/preloaded with the bone material.

The bone material comprises fully demineralized bone fibers and surface demineralized bone chips. The bone material may also comprise fibers, powder, chips, triangular prisms, spheres, cubes, cylinders, shards or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

The kit also includes fastening elements 44 that facilitate fixation of the bone implant to the surgical site. Fastening elements may include resorbable screws, resorbable tacks, adhesives, or a combination thereof. The fastening elements may also include, but are not limited to a bioadhesive or glue, cement, tape, tissue adhesives, a biological fastening element to promote tissue ingrowth such as a porous coating or a hydroxyapatite-tricalcium phosphate (HA/TCP) coating, multi-axial screws, sagittal angulation screws, pedicle screws, mono-axial screws, uni-planar screws, fixed screws, anchors, tissue penetrating screws, conventional screws, expanding screws, anchors, buttons, clips, snaps, friction fittings, compressive fittings, expanding rivets, staples, nails, adhesives, posts, connectors, and/or fixation plates. Alternatively, the fastening elements may comprise a material that becomes tacky upon wetting. Such a material may be, for example, a protein or gelatin based material. Tissue adhesives, including mussel adhesive proteins and cryanocrylates may be used to impart tackiness to the mesh material. In further examples, alginate or chitosan material may be used to impart tackiness to the mesh material. In further embodiments, an adhesive substance or material may be placed on a portion of the mesh material or in a particular region of the mesh material to anchor that portion or region of the mesh material in place at the surgical site.

The kit may also alternatively, or in addition to include the bone implants that are described below. In various embodiments, the kit may include additional parts along with the implant combined together to be used with implant and dilators (e.g., wipes, needles, syringes, etc.). The kit may include the mesh material in a first compartment. The second compartment may include a vial holding the bone material, diluent and any other instruments needed for the localized implant delivery. A third compartment may include gloves, drapes, wound dressings and other procedural supplies for maintaining sterility of the implanting process, as well as an instruction booklet, which may include a chart that shows how to implant the bone implant. A fourth compartment may include additional needles, fasteners, and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

Bone Implants

A bone implant 46 is provided, as shown in FIGS. 4 to 7, that is similar to bone implant 38 in FIGS. 1-3. The bone implant is configured for use in a posterolateral fusion procedure but may also be used in healing vertebral compression fractures, interbody fusion, minimally invasive procedures, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others.

Figure 4:
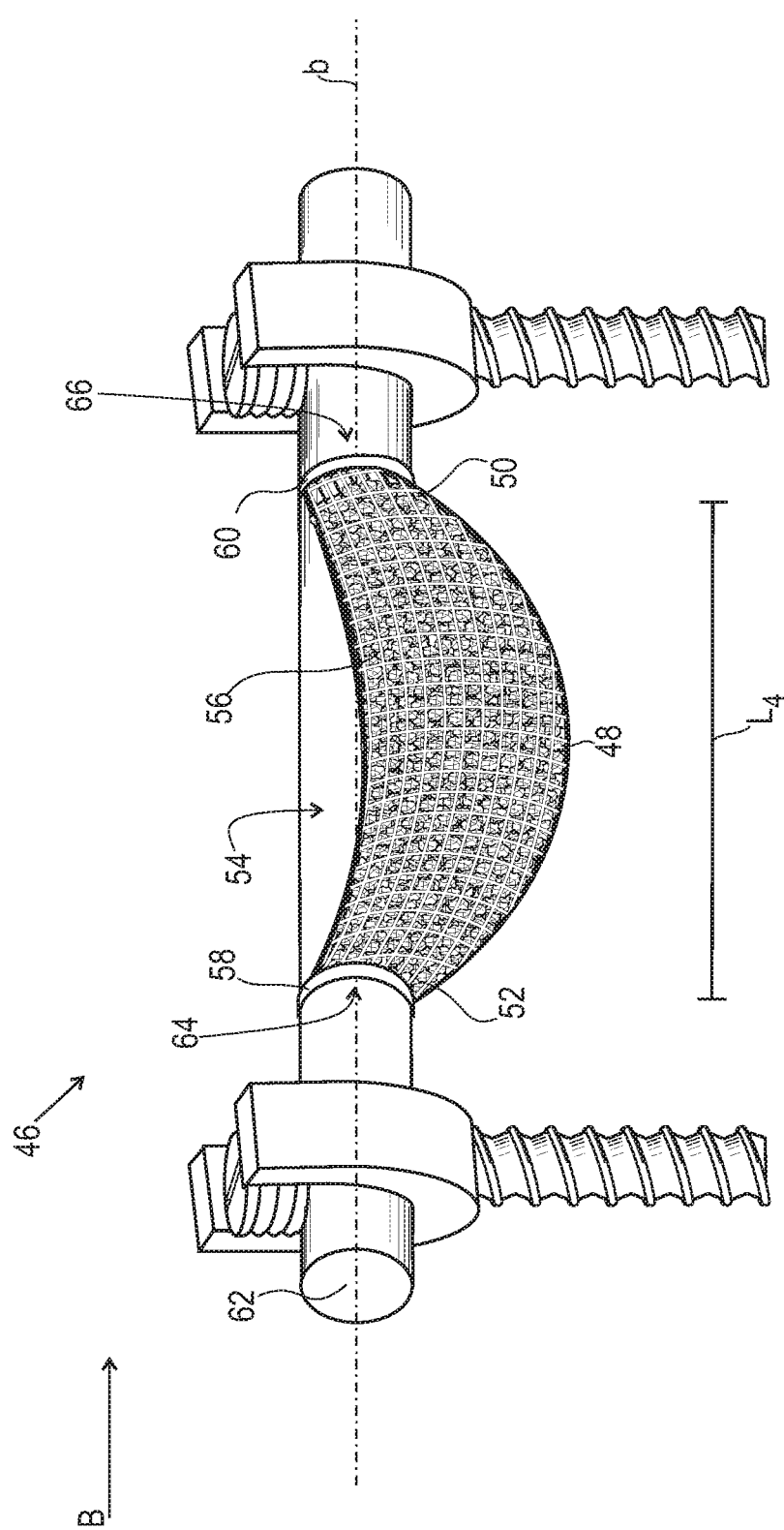
FIG. 4 is a perspective view of a bone implant comprising a mesh net and bone material that attaches to a spinal rod with grommets that are fixed to the mesh net.

The bone implant includes a mesh body 48 having a distal end 50 and a proximal end 52. A compartment 54 and a longitudinal axis b is disposed between the distal and proximal ends of the mesh body, and the compartment is configured to receive a bone material 56. In some embodiments, the bone implant is a mesh net and/or is hammock shaped, as shown in FIG. 4. In this configuration, the bone material is disposed within the compartment of the mesh body and/or on the outside of the mesh body. The mesh net and/or hammock shape bone implant may or may not enclose all of the graft material in its entirety.

The bone implant can be custom made before administration to the surgical site or the bone implant can be prefilled/preloaded with the bone material. The mesh body can be made from a resorbable natural or synthetic polymer including, but not limited to, at least one of poly(lactic acid) (PLA), poly(glycolic acid) (PGA), poly(lactic-co-glycolic acid) (PLGA), silk, or a combination thereof. The mesh body may include a selected weave pattern to impart flexibility and stretchable characteristics to the mesh. The mesh body can also be braided and/or knitted.

The mesh body may have varying degrees of permeability. It may be permeable, semi-permeable, or non-permeable. Permeability may be with respect to cells, to liquids, to proteins, to growth factors, to bone morphogenetic proteins, or other. In alternative embodiments, the mesh body may comprise a substantially solid structure, such as a polymer structure with a chamber, or a spun cocoon.

The mesh body itself can be a porous mesh such that fluid transfer and cell infiltration can occur so that osteoblasts can manufacture bone graft. The porous mesh body can have a pore size of from about 1 micron to about 2000 microns, from about 1 micron to about 1500 microns, from about 1 micron to about 1000 microns, from about 1 micron to about 500 microns, from about 1 micron to about 250 microns, from about 100 micron to about 2000 microns, from about 150 to about 1500 microns, from about 200 to about 1000 microns, from about 250 to about 500 microns. In some embodiments, the pore size can be about 1, 10, 20, 50, 80, 100, 120, 150, 180, 200, 220, 250, 280, 300, 350, 400, 450, 500, 550, 600, 650, 700, 750, 800, 850, 900, 950, 1000, 1250, 1450, 1650, 1850, and/or 2000 microns.

The mesh body includes a length $L_4$. The length of the mesh body may be from about 5 millimeters (mm) to about 180 mm, from about 10 millimeters to about 150 mm, from about 15 mm to about 130 mm, from about 20 mm to about 110 mm, from about 30 to about 100 mm, from about 40 mm to about 70 mm, or from about 50 mm to about 60 mm.

The bone implant also includes a first cylindrical member, such as a first grommet 58 disposed at or near the proximal end of the mesh body, and a second cylindrical member, such as a second grommet 60 disposed at or near the distal end of the mesh body. The first and second grommets are configured for engagement and alignment with longitudinal axis b and with a spinal rod 62 to facilitate containment and to prevent migration of the bone material at a surgical site. The bone implant may include more than one grommet at each end of the mesh body. For example, the bone implant may include 1, 2, 3, or 4 grommets at each end of the mesh body. The grommets may also be disposed on discrete regions of the mesh body such as on an outer perimeter of the mesh body.

The first grommet and the second grommet each comprise a through hole 64, 66, respectively, that are configured to receive screws 61, 63 to anchor the mesh material and/or are configured to engage an outer surface of the spinal rod. For example, as shown in FIG. 4, a user slidably or fixedly engages the grommets in a direction, as shown by arrow B, onto the spinal rod such that the grommets are in alignment with longitudinal axis b. In an alternative configuration, the spinal rod includes grooves and/or slots that are configured for engagement with the grommets such that the grommets can engage the spinal rod in a locked engagement.

The first and second grommets can be resorbable, and are configured for at least partial slidable engagement with the spinal rod. The resorbable grommets can be made from synthetic polymeric resorbable materials comprising poly (lactic acid) (PLA), poly(glycolic acid) (PGA), poly(lactic acid-glycolic acid) (PLGA), polydioxanone, polyvinyl alcohol (PVA), polyurethanes, polycarbonates, polyhydroxyalkanoates (polyhydroxybutyrates and polyhydroxyvalerates and copolymers), polysaccharides, polyhydroxyalkanoates, polyglycolide-co-caprolactone, polyethylene oxide, polypropylene oxide, polyglycolide-co-trimethylene carbonate, poly(lactic-co-glycolic acid), or a combination thereof.

The grommets can also be made from silk, or extracellular matrix including demineralized bone matrix, ligament, tendon tissue, or silk-elastin, elastin, collagen, cellulose, gelatin, chitosan, alginate, a ceramic with hydroxyapatite; a polymer comprising polyalkylenes, polyamides, polyesters, poly(glaxanone), poly(orthoesters), poly(pyrolic acid), poly (phosphazenes), or carbon fiber, metal fiber, polyetheretherketones (PEEK), non-resorbable polyurethanes, polyethers, polyethylene terephthalate, polyethylene, polypropylene, Teflon® or a combination thereof.

The grommets can be various sizes, including, but not limited to about 4 mm to about 50 mm, about 10 mm to about 40 mm, about 15 to about 30 mm, or about 20 to about 25 mm. In some embodiments, the grommets can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and/or 50 mm. The grommets can have a selected thickness, including, but not limited to about 1 mm to about 10 mm, about 1 mm to about 6 mm, about 1 mm to about 4 mm, about 4 mm to about 8 mm or about 6 mm to about 10 mm. In some embodiments, the grommets can be from about 1, 2, 3, 4, 5, 6, 7, 8, 9 or 10 mm in thickness. The grommets can be rigid and a fixed size. In alternative embodiments, the grommets can be elastic and be sized to fit various diameters of the rod.

The grommets can have a selected modulus of elasticity including from about $1\times10^2$ to about $6\times10^5$ dynes/cm$^2$, or $2\times10^4$ to about $5\times10^5$ dynes/cm$^2$, or $5\times10^4$ to about $5\times10^5$ dynes/cm$^2$.

In various embodiments, the polymer used in the grommets has a molecular weight, as shown by the inherent viscosity, from about 0.10 dL/g to about 1.2 dL/g or from about 0.10 dL/g to about 0.40 dL/g. Other IV ranges of the polymers in the depot include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, and about 1.8 to about 2.1 dL/g.

The grommets can have an outer surface having a selected texture, including, but not limited to smooth or rough, and may be coated or otherwise treated with a compound. For example, hydrogels, or other polymers, such as biocompatible and/or biodegradable polymers, may be used to coat the grommets. The grommets may also be coated with bone morphogenic proteins (BMPs), growth factors, antibiotics, angiogenesis promoting materials, bioactive agents or other actively releasing materials, as described herein.

Figure 6:
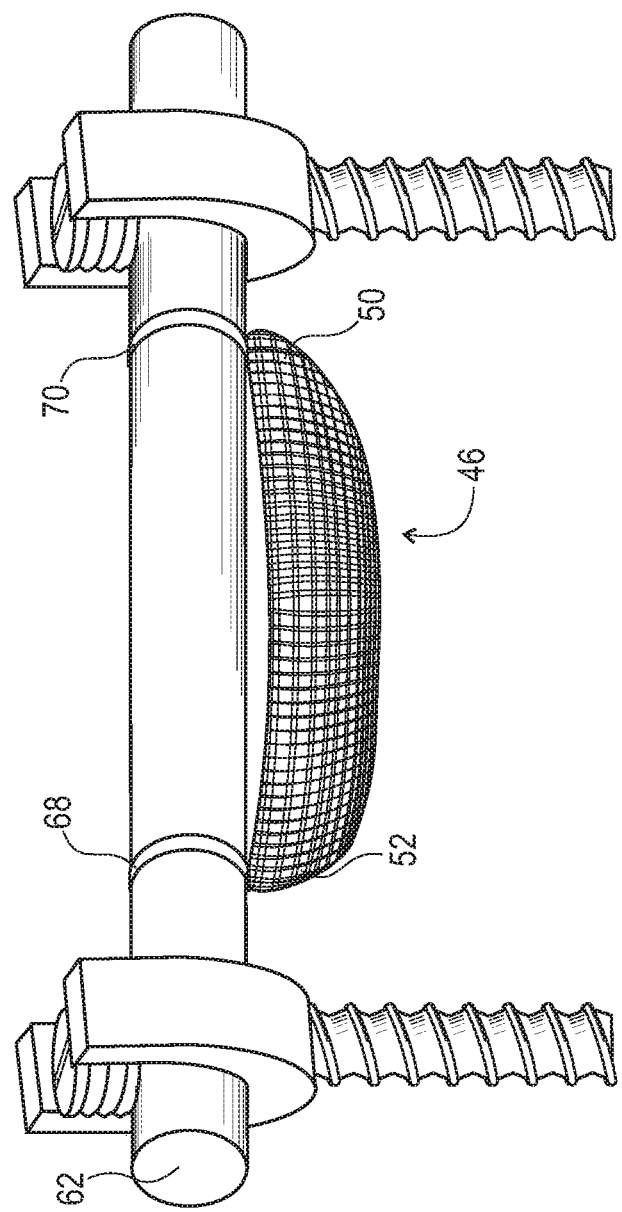
FIG. 6 is a perspective view of a bone implant comprising a closed mesh bag and bone material disposed within the mesh bag. The bone implant hangs from cylindrical members (e.g., loops) that are attached to a spinal rod.

In some embodiments, the bone implant may be shaped as a mesh bag, as shown in FIG. 6. The mesh bag can engage the spinal rod with alternative cylindrical members, such as, for example, a first loop 68 disposed at or near the proximal end of the mesh body and a second loop 70 disposed at or near the distal end of the mesh body. The first loop and the second loop are configured for engagement with the spinal rod, similar to the grommet engagement of the spinal rod, as described above. The loops can be made from any of the resorbable or non-resorbable materials described above with regard to the grommets. The loops can also be made from any natural or synthetic structure (tissue, protein, carbohydrate). Thus, the loops may be formed of a polymer (such as polyalkylenes (e.g., polyethylenes, polypropylenes, etc.), polyamides, polyesters, poly(glaxanone), poly(orthoesters), poly(pyrolicacid), poly(phosphazenes), polycarbonate, other bioabsorbable polymer such as Dacron or other known surgical plastics, a natural biologically derived material such as collagen, gelatin, chitosan, alginate, a ceramic (with bone-growth enhancers, hydroxyapatite, etc.), PEEK (polyether-etherketone), dessicated biodegradable material, metal, composite materials, a biocompatible textile (e.g., cotton, silk, linen), extracellular matrix components, tissues, or composites of synthetic and natural materials, or other.

Figure 7:
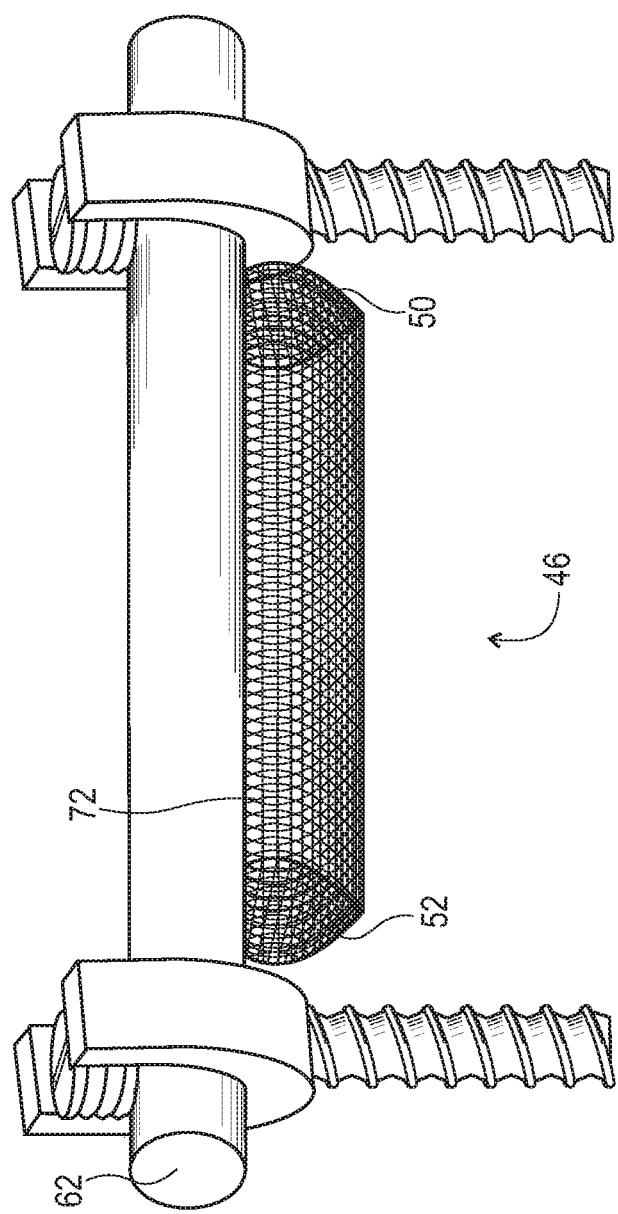
FIG. 7 is a perspective view of a bone implant comprising a mesh that is rigid, cannulated and semi-hemispherical. The mesh has a compartment to hold bone material. The bone implant abuts and adheres to the underside of a spinal rod.

In some embodiments, the mesh body of the bone implant may have a rigid and cannulated preformed shape, as shown in FIG. 7. In this configuration, the mesh body is rigid, and can be hemispherical, semi-hemispherical, hexagonal or a waterslide shape. There is a compartment in the mesh material to load the bone material. The bone implant is configured to abut and/or be adjacent to the spinal rod and can attach to the spinal rod via an adhesive 72. Suitable adhesives include, but are not limited to cyanoacrylates (such as histoacryl, B Braun, which is n-butyl-2 cyanoacrylate; or Dermabond, which is 2-octylcyanoacrylate); epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance.

Figure 5:
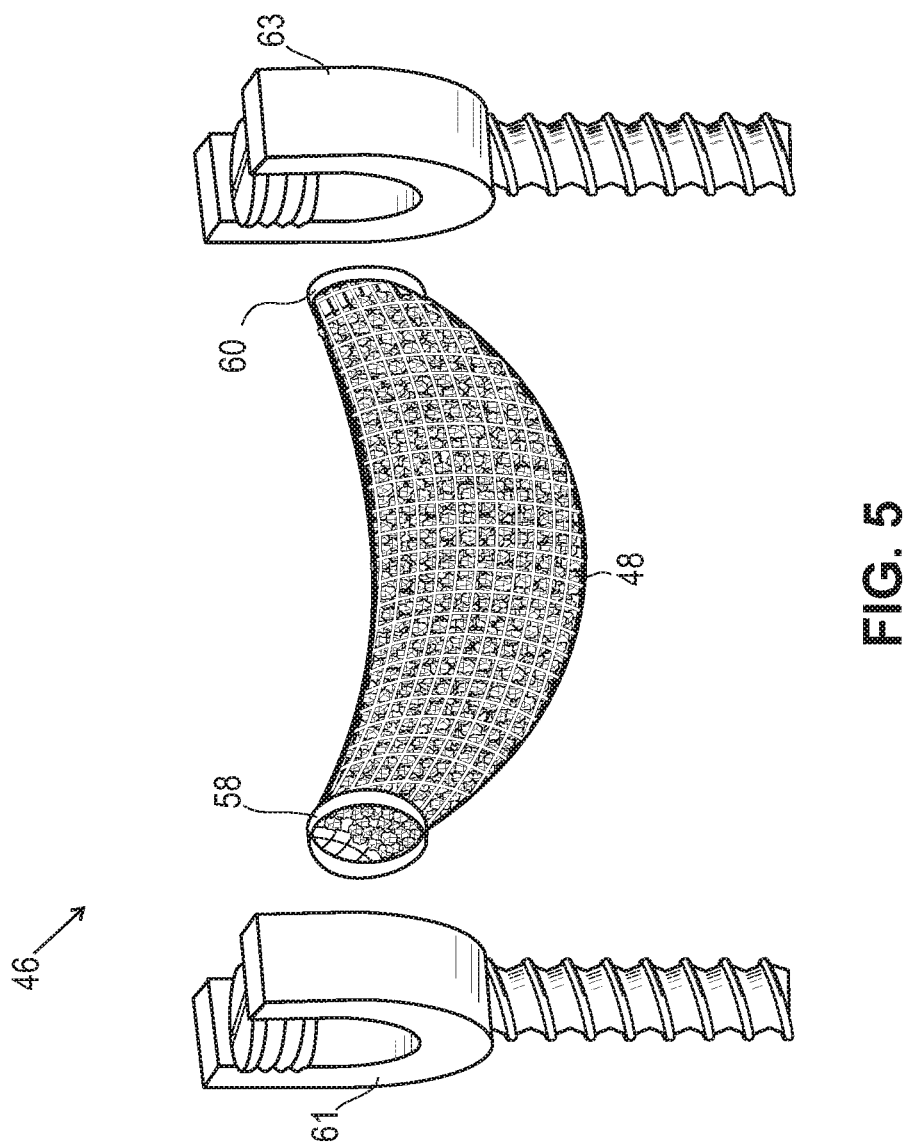
FIG. 5 is a perspective view of the mesh net of FIG. 4.

The bone implant may also be attached to the spinal rod via absorbable Velcro®. Grommets, and/or loops can engage the spinal rod with the bone implant in a similar manner as shown in FIGS. 4-6.

The mesh body of the bone implant may be in other shape configurations. For example, the mesh body may be formed as a ring, a cylinder, a cage, a rectangular shape, a suture-like wrap, a continuous tube, or any other configuration suitable to engage the rod. The mesh body can comprise one or a plurality of compartments that compliments its cannulated shape. For example, in a tubular embodiment, the tube may be formed into a plurality of compartments by tying a cord around the tube at one or more points, or by other suitable mechanism such as crimping, twisting, knotting, stapling, sewing, or other. The configuration of the mesh body may be determined by the substance to be provided within the mesh body. The mesh body can also be custom made before administration to the surgical site or the mesh can be prefilled/preloaded with the bone material at the manufacturer or shortly before surgery.

The bone material of the bone implant, in some embodiments, comprises fully demineralized bone fibers and surface demineralized bone chips. The bone material may also comprise fibers, powder, chips, triangular prisms, spheres, cubes, cylinders, shards or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

Figure 8:
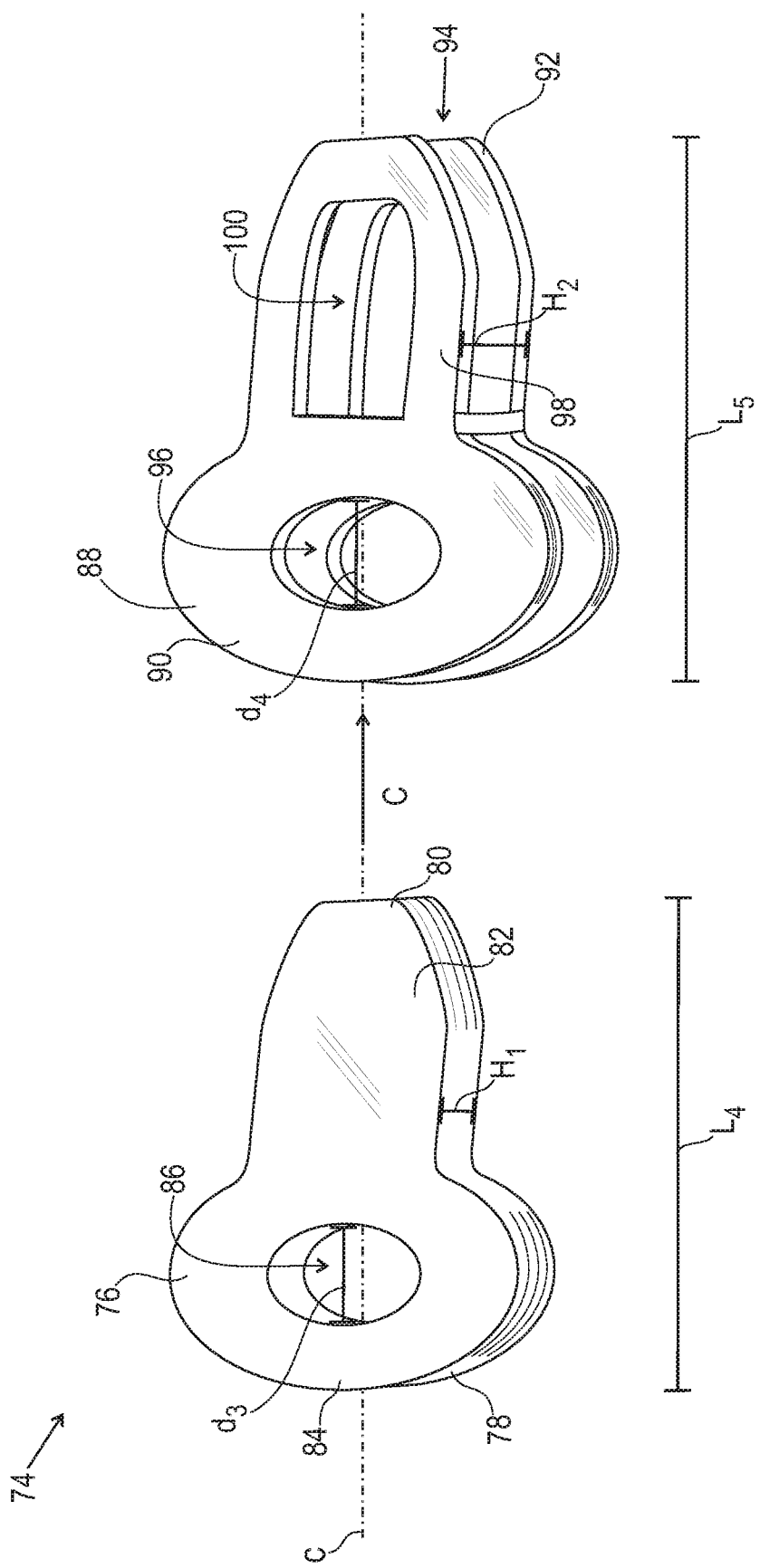
FIG. 8 is a perspective view of a bone implant comprising a bone material body and a bone material covering. The bone material body is configured for slidable engagement within the bone material covering, and the bone implant is configured for engagement with a bone fastener.
Figure 9:
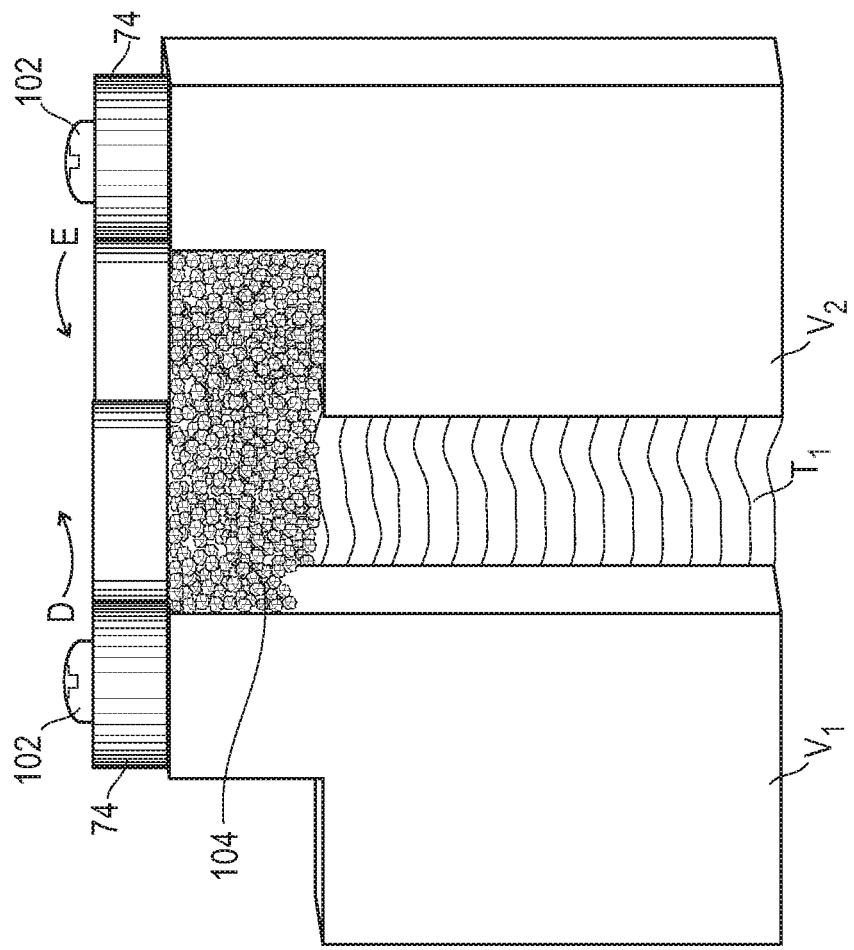
FIG. 9 is a side view of the bone implant of FIG. 8 that is disposed adjacent a first vertebra and is in a locking configuration with a second identical bone implant that is disposed adjacent a second vertebra. The bone implants are disposed adjacent to and contact the vertebrae via bone fasteners. The two bone implants create a bone lock at the surgical site.

Another embodiment of the bone implant 74 is provided, as shown in FIGS. 8 to 9. The bone implant is resorbable and is configured for use in a posterolateral fusion procedure but may also be used in healing vertebral compression fractures, interbody fusion, minimally invasive procedures, correction of adult or pediatric scoliosis, and others.

The bone implant includes a bone material body 76 comprising a proximal end 78 and a distal end 80. An elongated portion 82 and a longitudinal axis c is disposed between proximal and distal ends. The bone material body is configured for engagement with a bone material covering, as described below. The proximal end comprises a head portion 84 having a first opening 86 configured to receive a bone fastener. The first opening may have a selected diameter, $d_3$, such as, for example, from about 2 mm to about 10 mm, from about 2 mm to about 8 mm, from about 2 mm to about 6 mm, or from about 2 mm to about 4 mm. The diameter of the first opening may be about 2, 3, 4, 5, 6, 7, 8, 9 or 10 mm.

The bone material body has a selected length $L_4$, such as, for example, from about 10 mm to about 30 mm, from about 12 mm to about 20 mm, from about 14 mm to about 18 mm or from about 12 mm to about 16 mm. The length of the bone material body can be 10, 11, 12, 13, 14, 15, 16, 17, 18, 19, 20, 21, 22, 23, 24, 25, 26, 27, 28, 29 or 30 mm. The bone material body can have a selected height $H_1$, such as, for example, from about 4 mm to about 12 mm, from about 4 to about 10 mm, from about 4 mm to about 8 mm, from about 4 mm to about 6 mm. The height of the bone material body can be about 4, 5, 6, 7, 8, 9, 10, 11 or 12 mm.

The bone material body can be made of natural and/or synthetic bone material. The bone material can be, in some embodiments, fully demineralized bone fibers and surface demineralized bone chips. The bone material body may also comprise fibers, powder, chips, triangular prisms, spheres, cubes, cylinders, shards or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

The bone implant also includes a bone material covering 88 that is configured to at least partially enclose the bone material body. The bone material covering includes a proximal end 90 and a distal end 92. Longitudinal axis c and a channel 94 is disposed between proximal and distal ends. The channel is configured to slidably receive the proximal end and the distal end of the bone material body. For example, a user moves the bone material body in a direction, as shown in arrow C of FIG. 8, such that the bone material body is inserted into the channel of the bone material covering. The bone material covering partially encloses the bone material body such that a majority of the bone material body is covered however, there is an opening in the covering to allow influx of cells (e.g., osteoblasts, osteoclasts, etc.) to allow bone formation. In some embodiments, the bone material covering can fully enclose the bone material body, such that there are no separate openings other than the porosity of the bone material covering. The bone material covering includes a second opening 96 intersecting with and transverse to the channel. The second opening is configured to align with the first opening of the bone material body and to receive a bone fastener when the bone material body is slidably received in the channel of the bone material covering. The second opening may have a selected diameter, $d_4$, such as, for example, from about 2 mm to about 10 mm, from about 2 mm to about 8 mm, from about 2 mm to about 6 mm, or from about 2 mm to about 4 mm. The diameter of the second opening may be about 2, 3, 4, 5, 6, 7, 8, 9 or 10 mm. The diameter $d_3$ of the first opening may be the same size as the diameter $d_4$ of the second opening, or the diameter $d_4$ of the second opening may be larger than the diameter $d_3$ of the first opening.

The bone material covering comprises an elongated covering portion 98. The elongated portion of the bone material body corresponds to the elongated covering portion of the bone material covering such that the bone material body is completely enclosed by the bone material covering. A third opening 100 is configured to facilitate release of the bone material that comprises the bone material body or release of additional bone material that is disposed within the third opening and/or to allow influx of cells (e.g., osteoblasts, osteoclasts, etc.). The third opening can be variously shaped and can be a circle, semi-circle, square, diamond, oval, rectangle, horseshoe, triangle, pentagon, hexagon, crescent, kite, heptagon, octagon, or decagon shaped. The third opening can be arcuate, concave, partially concave, convex, partially convex or linear and may comprise more than one opening.

The elongated covering portion of the bone material covering has a surface area that is configured to prevent migration of bone material from the surgical site. Reduction in surface area can affect cell attachment, mobility, proliferation, and differentiation. The surface area of the elongated covering portion may be textured and/or chemically modified to increase or decrease the surface area of the elongated covering portion. The elongated covering portion may also be lyophilized. The surface's affinity for growth factors and release kinetics of growth factors from the surface may also be altered.

The bone material covering has a selected length $L_5$, such as, for example, from about 10 mm to about 35 mm, from about 12 mm to about 25 mm, from about 14 mm to about 20 mm or from about 16 mm to about 18 mm. The length of the bone material body can be 10, 11, 12, 13, 14, 15, 16, 17, 18, 19, 20, 21, 22, 23, 24, 25, 26, 27, 28, 29, 30, 31, 32, 33, 34 or 35 mm. The bone material covering length $L_5$ is greater than the bone material body length $L_4$. The bone material body can have a selected height $H_2$, such as, for example, from about 6 mm to about 18 mm, from about 6 to about 16 mm, from about 6 mm to about 14 mm, or from about 6 mm to about 12 mm. The height of the bone material body can be about 6, 7, 8, 9, 10, 11, 12, 13, 14, 15, 16, 17 or 18 mm. The bone material covering height $H_2$ is greater than the bone material body $H_1$ height.

The bone material covering can be made from the same or different material than the bone material body. The bone material covering can be made of fully demineralized bone fibers and surface demineralized bone chips. The bone material body may also comprise fibers, powder, chips, triangular prisms, spheres, cubes, cylinders, shards or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

The bone material covering can also be made from biopolymers, including, but not limited to, poly (alpha-hydroxy acids), poly (lactide-co-glycolide) (PLGA), polylactide (PLA), polyglycolide (PG), poly(glycolic acid) (PGA), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof.

The bone material covering may not be fully biodegradable or resorbable. For example, the bone material covering may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon device, glass device, plastics, ceramics, methacrylates, poly (N-isopropylacrylamide), PEO-PPO-PEO (pluronics) or combinations thereof.

In some embodiments, the bone implant is configured for locking engagement with a second bone implant 74 at their ends and/or elongated covering portions, as shown in FIG. 9. Each of the first and second openings of the bone implants receive a bone fastener 102 that fixedly engages with vertebrae V, such as vertebra V1 and V2 respectively. The elongated covering portion of the bone implant, along with the elongated covering portion of the second bone implant extend in directions shown by arrows D and E, such that the bone implant and the second bone implant create a locked engagement with bone material 104 and/or side walls of the bone implant. The side walls, in some embodiments, contact each bone implant and lock and confine the bone material to the surgical site. This locked engagement can create a bone lock, and the engagement of the ends, side walls and/or the elongated covering portions can be offset and/or overlapped. This stacking arrangement of the bone implants facilitates packing of additional bone material into a surgical site of a patient and above tissue $T_1$. Alternatively or in addition to, the bone implants are configured for use with bone implant 46 comprising a mesh body 48, as described in FIG. 5. The additional bone material may comprise of the same or different material as the bone material described herein.

Mesh Formulations

The mesh material and/or mesh body of the instant application may be configured from woven threads that are configured to allow ingrowth of cells while also retaining the bone material within the compartment of the bone implant. The threads of the mesh may have a predetermined thickness of about 0.01 mm to about 2.0 mm, about 0.05 mm to about 1.0 mm, or about 0.1 to about 0.5 mm. The thickness of the threads may be uniform along the length of each thread, or varied across the length of each thread. In some embodiments, some threads have a greater thickness than other threads. The threads may be sized to allow for customizable pore sizes between the threads. In some embodiments, the bone implant is configured to facilitate transfer of substances and/or materials surrounding the surgical site. Upon implantation to a surgical site, the bone implant may participate in, control, or otherwise adjust, or may allow penetration of the mesh by surrounding materials, such as cells or tissue.

The mesh may be sized according to the needs of a particular application. For example, the mesh may include dimensions between about 1 mm to about 100 mm in diameter. In some embodiments, the mesh includes a diameter of about 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, or 100 mm. In some embodiments, the mesh includes a length or depth between about 0.1 cm to about 10 cm. In some embodiments, the mesh includes a length or depth of about 1 cm, 2 cm, 3 cm, 4 cm, 5 cm, 6 cm, 7 cm, 8 cm, 9 cm, or 10 cm.

In some embodiments, the mesh can have selected dimensions, such as, for example, a diameter of 0.5 cm and a length of 0.1 cm, providing a volume of 0.02 cc. In other embodiments, the mesh can have a diameter of 1 cm and a length of 1 cm, providing a volume of 0.79 cc. In yet other embodiments, a mesh bag has a diameter of 1.5 cm and length of 3 cm, providing a volume of 5.3 cc.

The shape, mesh size, thickness, and other structural characteristics, of the mesh material and/or mesh body, for example, architecture, may be customized for the desired application. For example, to optimize cell or fluid migration through the mesh, the pore size may be optimized for the viscosity and surface tension of the fluid or the size of the cells. For example, pore sizes between threads on the order of approximately 100-200 μm may be used if cells are to migrate through the mesh. In other embodiments, wave-shaped threads may be extruded to have larger peaks and crests and the size of the pores may be larger. For example, in some embodiments, the pore size between threads may be about 0.1 mm to about 5 mm, about 0.5 mm to about 3 mm, or about 1 mm to about 2 mm. Mesh size may be controlled by physically weaving strands and by controlling the thickness of threads.

The mesh may have varying degrees of permeability across its surface. It may be permeable, semi-permeable, or non-permeable. Permeability may be with respect to cells, to liquids, to proteins, to growth factors, to bone morphogenetic proteins, or other. In further embodiments, the material may be braided.

The mesh material and/or mesh body may have any suitable configuration. For example, the mesh material and/or mesh body can have a variety of shapes, such as, for example, a ring, a cylinder, a cage, a rectangular shape, a suture-like wrap, a continuous tube, or other configurations. The mesh material and/or mesh body may be formed as a thin tube designed to be inserted through catheters or an introducer tube; a rectangular shape designed to fit adjacent to spinal processes for posterolateral spine fusion; a cube; a rectangular prism like structure designed to fit between vertebral bodies or within cages for interbody spinal fusion; a tube-like shape; relatively flat shapes; rectangular shapes; structures pre-shaped to fit around various implants (e.g., dental, doughnut with hole for dental implants); or relatively elastic ring-like structures that will stretch and then conform to shapes (e.g. rubber band fitted around processes).

Additionally, in some embodiments, the flexible character of the mesh allows for the mesh material and/or mesh body to be manipulated into a plurality of compartments. For example, in a tubular embodiment, the tube may be formed into a plurality of compartments by tying a cord around the tube at one or more points, or by other suitable mechanism such as crimping, twisting, knotting, stapling, or sewing.

An example of the mesh material and/or mesh body can be the MAGNIFUSE® Bone Graft, available from Medtronic, Inc. which comprises surface demineralized bone chips mixed with non-demineralized cortical bone fibers or fully demineralized bone fibers sealed in an absorbable poly(glycolic acid) (PGA) mesh implant or bag or pouch.

In certain embodiments, a bone void can be filled by mesh material and/or mesh body containing bone material. A compartment within mesh material and/or mesh body can be at least partially filled with a bone repair substance. In various embodiments, at least partially filled as used herein, can mean that a percentage of the volume of a compartment or hollow interior region is at least 70% occupied, at least 75% occupied, at least 80% occupied, at least 85% occupied, at least 90% occupied, at least 95% occupied, or 100% occupied. Mesh material and/or mesh body can be inserted into an opening in the defect until the defect is substantially filled. In various embodiments, substantially filled, as used herein, can mean that a percentage of the volume of a defect is at least 70% occupied, at least 75% occupied, at least 80% occupied, at least 85% occupied, at least 90% occupied, at least 95% occupied, or 100% occupied.

In some embodiments, mesh material and/or mesh body may be labeled. Such labeling may be done in any suitable manner and at any suitable location on the mesh material and/or mesh body. In some embodiments, labeling may be done by using a silk screen printing, using an altered weaving or knotting pattern, by using different colored threads, or other means. The labeling may indicate information regarding mesh material and/or mesh body. Such information might include a part number, donor ID number, number, lettering or wording indicating order of use in the procedure or implant size, etc.

The mesh material and/or mesh body may comprise a penetrable material at a first compartment configured for placement adjacent bone and a substantially impenetrable material at a second compartment configured for placement adjacent soft tissue. For example, the pore size between the threads at a first region of the mesh material and/or mesh body may be sized large enough to allow cell migration through the mesh material and/or mesh body, but the pore size between the threads at a second region of the mesh material and/or mesh body may be sized small enough (or may include a lack of pores altogether) to prevent cell migration. Alternatively, the material of the mesh material and/or mesh body may have a uniform configuration such that adjacent compartments may have substantially identical characteristics. By way of example only, the mesh material and/or mesh body may have a porous surface that is positioned adjacent bone, and a separate or opposite surface that has a generally impenetrable surface that is positioned adjacent soft tissue. Alternatively, the mesh material and/or mesh body may have one compartment that comprises a porous material, and a second compartment that comprises a substantially impenetrable material.

For either single and multi-compartment bone implants, the mesh material and/or mesh body may be closed after filling substances. Accordingly, the bone implant may be provided in an unfilled, unsealed state. After a substance for delivery is placed in the bone implant, the mesh material and/or mesh body of the bone implant may be permanently or temporarily closed. Temporary closure may be by tying, fold lock, cinching, or other means. A temporarily closed bone implant can be opened without damaging the mesh material and/or mesh body during surgical implantation to add or remove substances in the bone implant.

Suitable adhesives for use for closing the mesh material and/or mesh body of the bone implant may include, for example, cyanoacrylates (such as histoacryl, B Braun, which is n-butyl-2 cyanoacrylate; or Dermabond, which is 2-octylcyanoacrylate); epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance. Adhesives may be selected for use based on their bonding time; for example, in some circumstances, a temporary adhesive may be desirable, for example, for fixation during the surgical procedure and for a limited time thereafter, while in other circumstances a permanent adhesive may be desired. Where the compartment is made of a material that is resorbable, the adhesive can be selected that would adhere for about as long as the material is present in the body.

In some embodiments, biological attachment may be via mechanisms that promote tissue ingrowth such as by a porous coating or a hydroxyapatite-tricalcium phosphate (HA/TCP) coating. Generally, hydroxyapatite bonds by biological effects of new tissue formation. Porous ingrowth surfaces, such as titanium alloy materials in a beaded coating or tantalum porous metal or trabecular metal may be used and facilitate attachment at least by encouraging bone to grow through the porous implant surface. These mechanisms may be referred to as biological attachment mechanisms. In some embodiments, the bone implant may be attached to a tissue structure through a wrap, a suture, a wire, a string, an elastic band, a cable or a cable tie, or a combination thereof.

In other embodiments, suitable materials that form the mesh material and/or mesh body of the bone implant include natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly(lactic acid) (PLA), poly(glycolic acid) (PGA), poly(lactic acid-glycolic acid) (PLGA), polydioxanone, PVA, polyurethanes, polycarbonates, and others.

In various embodiments, the mesh material and/or mesh body comprises a polymer matrix. In some embodiments, DBM fibers and/or DBM powder are suspended in the polymer matrix to facilitate transfer of cells into and out of the mesh bag to induce bone growth at the surgical site. In other embodiments, the mesh material and/or mesh body further comprises mineralized bone fibers suspended in a polymer matrix. In some embodiments, the DBM powder is suspended in the polymer matrix between the DBM fibers and the mineralized bone fibers. In some embodiments, the DBM powder is suspended between the DBM fibers in the polymer matrix so as to reduce and/or eliminate gaps that exist between the fibers. In some embodiments, the DBM powder is suspended between the DBM fibers in the polymer matrix to improve osteoinductivity for facilitating bone fusion, for example, interspinous process fusion.

In some embodiments, the polymer matrix comprises a bioerodible, a bioabsorbable, and/or a biodegradable biopolymer that may provide immediate release or sustained release. Examples of suitable sustained release biopolymers include, but are not limited to, poly (alpha-hydroxy acids), poly (lactide-co-glycolide) (PLGA), polylactide (PLA), polyglycolide (PG), polyethylene glycol (PEG), conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers. SAIB (sucrose acetate isobutyrate), or combinations thereof. mPEG and/or PEG may be used as a plasticizer for PLGA, but other polymers/ excipients may be used to achieve the same effect. mPEG imparts malleability to the polymer. In some embodiments, these biopolymers may also be coated on the mesh material and/or mesh body to provide a desired release profile or ingrowth of tissue. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the substance from the bone implant. In some embodiments, the range of the coating on the mesh material and/or mesh body ranges from about 5 microns to about 250 microns or 5 microns to about 200 microns.

In some embodiments, various components of the mesh material and/or mesh body comprise poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

In some embodiments, the mesh material and/or mesh body further comprises bone morphogenic proteins (BMPs), growth factors, antibiotics, angiogenesis promoting materials, bioactive agents or other actively releasing materials.

The mesh material and/or mesh body may be used to deliver a substance comprising any suitable biocompatible material. In specific embodiments, the mesh material and/or mesh body may be used to deliver surface demineralized bone chips, optionally of a predetermined particle size, fully demineralized bone fibers, optionally pressed, and/or allograft. For embodiments where the substance is a biologic, the substance may be autogenic, allogenic, xenogenic, or transgenic. Other suitable materials that may be positioned in the mesh material and/or mesh body include, for example, protein, nucleic acid, carbohydrate, lipids, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, DBM, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above.

In accordance with some embodiments, the material to be positioned in the hollow compartment of the mesh material and/or mesh body may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; DBM powder; collagen, insoluble collagen derivatives, etc., and soluble solids and/or liquids dissolved therein; anti-AIDS substances; anti-cancer substances; anti-microbials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements, co-factors for protein synthesis, endocrine tissue or tissue fragments; synthesizers; enzymes such as alkaline phosphatase, collagenase, peptidases, oxidases and the like; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other member; tissue transplants; autogenous tissues such as blood, serum, soft tissue, bone marrow, or the like; bioadhesives; bone morphogenetic proteins (BMPs including BMP-2); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, for example, interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, for example, fatty acid esters such as laureate, myristate and stearate monoesters of polyethylene glycol, enamine derivatives, alpha-keto aldehydes; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

The material may have functional characteristics. Alternatively, other materials having functional characteristics may be incorporated into the mesh material and/or mesh body. Functional characteristics may include radiopacity, bacteriocidity, source for released materials, tackiness, etc. Such characteristics may be imparted substantially throughout the mesh material and/or mesh body or at only certain positions or portions of the mesh material and/or mesh body.

Suitable radiopaque materials include, for example, ceramics, mineralized bone, ceramics/calcium phosphates/calcium sulfates, metal particles, fibers, and iodinated polymer (see, for example, WO/2007/143698). Polymeric materials may be used to form the mesh material and/or mesh body and be made radiopaque by iodinating them, such as taught for example in U.S. Pat. No. 6,585,755, herein incorporated by reference in its entirety. Other techniques for incorporating a biocompatible metal or metal salt into a polymer to increase radiopacity of the polymer may also be used. Suitable bacteriocidal materials may include, for example, trace metallic elements. In some embodiments, trace metallic elements may also encourage bone growth.

In some embodiments, the mesh material and/or mesh body may comprise a material that becomes tacky upon wetting. Such material may be, for example, a protein or gelatin based material. Tissue adhesives, including mussel adhesive proteins and cryanocrylates, may be used to impart tackiness to the mesh material and/or mesh body. In further examples, alginate or chitosan material may be used to impart tackiness to the mesh material and/or mesh body. In further embodiments, an adhesive substance or material may be placed on a portion of the mesh material and/or mesh body or in a particular region of the mesh material and/or mesh body to anchor that portion or region of the mesh material and/or mesh body in place at a surgical site.

Bone Material

In various embodiments, the bone material may be particulated such as, for example, in bone chips, powder or fiber form. If the bone is demineralized, the bone may be made into a particulate before, during or after demineralization. In some embodiments, the bone may be monolithic and may not be a particulate.

The bone may be milled and ground or otherwise processed into particles of an appropriate size before or after demineralization. The particles may be particulate (for example, powder) or fibrous. The terms milling or grinding are not intended to be limited to production of particles of a specific type and may refer to production of particulate or fibrous particles. In certain embodiments, the particle size may be greater than 25 microns, such as ranging from about 25 to about 2000 microns, or from about 25 to about 500 microns or from about 200 to about 1000 microns. In some embodiments, the size of the bone particles are less than 100 microns. In some embodiments, the size of the bone particles are less than 500 microns.

After grinding, the bone particles may be sieved to select those particles of a desired size. In certain embodiments, the particles may be sieved though a 25 micron sieve, a 50 micron sieve, a 75 micron sieve, a 100 micron sieve, a 125 micron sieve, a 150 micron sieve, a 175 micron sieve and/or a 200 micron sieve.

In some embodiments, the bone material comprises DBM and/or mineralized bone. In some embodiments, the size of the bone material is less than 25 microns. In some embodiments, the bone material particle size is about 1, 2, 3, 4, 5, 6, 7, 8, 9, 10, 11, 12, 13, 14, 15, 16, 17, 18, 19, 20, 21, 22, 23, 24 and/or 25 microns.

In various embodiments, the bone powder, chips and/or the DBM and/or mineralized bone fibers have a sticky outer surface such that the bone material can adhere to DBM and/or mineralized bone fibers. In various embodiments, the bone powder is naturally sticky. In some embodiments, an adhesive agent is applied to the bone powder and/or the bone fibers comprising a bio-adhesive, glue, cement, cyanoacrylate, silicones, hot melt adhesives and/or cellulosic binders. In various embodiments, the adhesive may be applied to the surface of the bone powder by spraying or brushing. In some embodiments, a charge is applied to the fibers and an opposite charge is applied to the bone powder, (i.e., the technique of electrostatic precipitation). The bone powder will be attracted to, and tenaciously adhere to, the surface of the fiber. Any of these application techniques can be repeated one or more times to build up a relatively thick layer of adherent bone powder on the surface of the fibers.

The bone powder can be applied directly to the DBM fiber and/or fully mineralized fiber, chips and the mixture can be disposed in the mesh material and/or mesh body. In some embodiments, the bone material inserted into the mesh material and/or mesh body contains pores having a pore size from about 0.5 to about 2,000 microns. In some embodiments, bone material inserted into the mesh material and/or mesh body contains pores having a pore size of from about 0.5, 5, 50, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950 to about 2,000 microns. In some embodiments, the pore size of the bone material is uniform. In some embodiments, the pore size of bone material is non-uniform and includes various pore sizes in the range from 0.5 to about 2,000 microns. Alternatively, the DBM fibers, chips, and DBM powder can be placed in a polymer (for example, collagen) and inserted into a porous biodegradable graft body (for example, a pouch, container, mesh material and/or mesh body, and the like).

Following shaving, milling or other technique whereby they are obtained, the bone material is subjected to demineralization in order to reduce its inorganic content to a very low level, in some embodiments, to not more than about 5% by weight of residual calcium and to not more than about 1% by weight of residual calcium. Demineralization of the bone material ordinarily results in its contraction to some extent.

Bone used in the methods described herein may be autograft, allograft, or xenograft. In various embodiments, the bone may be cortical bone, cancellous bone, or cortico-cancellous bone. While specific discussion is made herein to demineralized bone matrix, bone matrix treated in accordance with the teachings herein may be non-demineralized, demineralized, partially demineralized, or surface demineralized. This discussion applies to demineralized, partially demineralized, and surface demineralized bone matrix. In one embodiment, the demineralized bone is sourced from bovine or human bone. In another embodiment, demineralized bone is sourced from human bone. In one embodiment, the demineralized bone is sourced from the patient's own bone (autogenous bone). In another embodiment, the demineralized bone is sourced from a different animal (including a cadaver) of the same species (allograft bone).

Any suitable manner of demineralizing the bone may be used. Demineralization of the bone material can be conducted in accordance with known conventional procedures. For example, in a preferred demineralization procedure, the bone materials useful for the implantable composition of this application are subjected to an acid demineralization step that is followed by a defatting/disinfecting step. The bone material is immersed in acid over time to effect its demineralization. Acids which can be employed in this step include inorganic acids such as hydrochloric acid and organic acids such as peracetic acid, acetic acid, citric acid, or propionic acid. The depth of demineralization into the bone surface can be controlled by adjusting the treatment time, temperature of the demineralizing solution, concentration of the demineralizing solution, agitation intensity during treatment, and other applied forces such as vacuum, centrifuge, pressure, and other factors such as known to those skilled in the art. Thus, in various embodiments, the bone material may be fully demineralized, partially demineralized, or surface demineralized.

After acid treatment, the bone is rinsed with sterile water for injection, buffered with a buffering agent to a final predetermined pH and then finally rinsed with water for injection to remove residual amounts of acid and buffering agent or washed with water to remove residual acid and thereby raise the pH. Following demineralization, the bone material is immersed in solution to effect its defatting. A defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses Ordinarily at least about 10 to 40 weight percent by weight of water (i.e., about 60 to 90 weight percent of defatting agent such as alcohol) should be present in the defatting/disinfecting solution to produce optimal lipid removal and disinfection within the shortest period of time. The concentration range of the defatting solution is from about 60 to 85 weight percent alcohol or about 70 weight percent alcohol.

Further in accordance with this application, the DBM material can be used immediately for preparation of the bone implant or it can be stored under aseptic conditions, advantageously in a critical point dried state prior to such preparation. In one embodiment, the bone material can retain some of its original mineral content such that the composition is rendered capable of being imaged utilizing radiographic techniques.

In various embodiments, this application also provides bone matrix compositions comprising critical point drying (CPI)) fibers DBM includes the collagen matrix of the bone together with acid insoluble proteins including bone morphogenic proteins (BMPs) and other growth factors. It can be formulated for use as granules, gels, sponge material or putty and can be freeze-dried for storage. Sterilization procedures used to protect from disease transmission may reduce the activity of beneficial growth factors in the DBM DBM provides an initial osteoconductive matrix and exhibits a degree of osteoinductive potential, inducing the infiltration and differentiation of osteoprogenitor cells from the surrounding tissues.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1. IGF-2. BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In various embodiments, the DBM provided in the kits, implants and methods described in this application is prepared from elongated bone fibers which have been subjected to critical point drying (CPD). The elongated CPD bone fibers employed in this application are generally characterized as having relatively high average length to average width ratios, also known as the aspect ratio. In various embodiments, the aspect ratio of the elongated bone fibers is at least from about 50:1 to at least about 1000:1. Such elongated bone fibers can be readily obtained by any one of several methods, for example, by milling or shaving the surface of an entire bone or relatively large section of bone.

In other embodiments, the length of the fibers can be at least about 3.5 cm and average width from about 20 mm to about 1 cm. In various embodiments, the average length of the elongated fibers can be from about 3.5 cm to about 6.0 cm and the average width from about 20 mm to about 1 cm. In other embodiments, the elongated fibers can have an average length from about 4.0 cm to about 6.0 cm and an average width from about 20 mm to about 1 cm.

In yet other embodiments, the diameter or average width of the elongated fibers is, for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In another embodiment, the aspect ratio of the fibers can be from about 50:1 to about 950.1, from about 50:1 to about 750:1, from about 50.1 to about 500-1, from about 50:1 to about 250.1; or from about 50.1 to about 100:1. Fibers according to this disclosure can have an aspect ratio from about 50:1 to about 1000:1, from about 50:1 to about 950:1, from about 50:1 to about 750-1, from about 50:1 to about 600:1, from about 50.1 to about 350.1, from about 50:1 to about 200:1, from about 50:1 to about 100:1, or from about 50:1 to about 75:1.

In some embodiments, the chips to fibers ratio is about 90:10, 80.20, 75:25, 7030, 60:40, 50:50, 40:60, 30:70, 25:75, 20:80 and/or 10:90. In various embodiments, a surface demineralized chips to fibers ratio is about 90:10, 80:20, 75:25, 70:30, 60:40, 50:50, 40:60, 30:70, 25:75, 20:80 and/or 10:90. In some embodiments, a surface demineralized chips to fully demineralized fibers ratio is about 90:10, 80:20, 75:25, 70:30, 60:40, 50:50, 40:60, 30:70, 25:75, 20:80 and/or 10:90.

In some embodiments, the DBM fibers have a thickness of about 0.5-4 mm. In various embodiments, the DBM fibers have a thickness of about 0.5, 0.6, 0.7, 0.8, 0.9, 1, 1.5, 2, 2.5, 3, 3.5 and/or 4 mm. In various embodiments, the ratio of DBM fibers to DBM powder is about 40:60 to about 90:10 W/W, W/V or V/V. In some embodiments, the ratio of mineralized bone fibers to DBM powder is about 25:75 to about 75:25 W/W, W/V or V/V. In various embodiments, the bone implant comprises DBM fibers and mineralized fibers in a ratio of 40:60 to about 90:10 W/W, W/V or V/V. In some embodiments, the DBM fibers to DBM powder ratio, mineralized bone fibers to DBM powder ratio and/or the DBM fibers and mineralized fibers ratio is from 5:95 to about 95:5 W/W, W/V or V/V. In some embodiments, the DBM fibers to DBM powder ratio, mineralized bone fibers to DBM powder ratio and/or the DBM fibers and mineralized fibers ratio is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 W/W, W/V or V/V.

In some embodiments, the bone material comprises demineralized bone material comprising demineralized bone, fibers, powder, chips, triangular prisms, spheres, cubes, cylinders, shards or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

In various embodiments, the bone material comprises fully DBM fibers and surface demineralized bone chips. In some embodiments, the ratio of fully DBM fibers to surface demineralized bone chips is from 5:95 to about 95:5 fibers to chips. In some embodiments, the ratio of fully DBM fibers to surface demineralized bone chips is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 fibers to chips. In various embodiments, the fully DBM fibers have a thickness of about 0.5-4 mm. In various embodiments, the fully DBM fibers have a thickness of about 0.5, 0.6, 0.7, 0.8, 0.9, 1, 1.5, 2, 2.5, 3, 3.5 and/or 4 mm.

In various embodiments, the fibers and/or the powder is surface DBM. In some embodiments, the fibers and/or the powder is surface DBM cortical allograft. In various embodiments, surface demineralization involves surface demineralization to at least a certain depth. For example, the surface demineralization of the allograft can be from about 0.25 mm, 0.5 mm, 1 mm, 1.5 mm, 2.0 mm, 2.5 mm, 3.0 mm. 3.5 mm, 4 mm, 4.5 mm, to about 5 mm. The edges of the bone fibers and/or powder may further be machined into any shape or to include features such as grooves, protrusions, indentations, etc., to help improve fit and limit any movement or micromotion to help fusion and/or osteoinduction to occur.

To prepare the osteogenic DBM, a quantity of fibers is combined with a biocompatible carrier to provide a demineralized bone matrix.

DBM typically is dried, for example via lyophilization or solvent drying, to store and maintain the DBM in active condition for implantation. Moreover, each of these processes is thought to reduce the overall surface area structure of bone. As may be appreciated, the structural damage of the exterior surface reduces the overall surface area. Physical alterations to the surface and reduction in surface area can affect cell attachment, mobility, proliferation, and differentiation. The surface's affinity for growth factors and release kinetics of growth factors from the surface may also be altered.

Accordingly, in some embodiments, methods for drying bone to store and maintain the bone in active condition for implantation that maintains or increases the surface area of the bone are provided. In one embodiment, the bone matrix is treated using a critical point drying technique, thereby reducing destruction of the surface of the bone. While specific description is made to critical point drying, it is to be appreciated that, in alternative embodiments, super critical point treatment may be used. In various embodiments utilizing CPD, a percentage of collagen fibrils on the surface of the bone are non-denatured after drying to a residual moisture content of approximately 15% or less. In some embodiments, after drying, the bone matrix has a residual moisture content of approximately 8% or less. In some embodiments, after drying, the bone matrix has a residual moisture content of approximately 6% or less. In some embodiments, after drying, the bone matrix has a residual moisture content of approximately 3% or less.

Evaporative drying and freeze drying of specimens can cause deformation and collapse of surface structures, leading to a decrease in surface area. Without wishing to be bound by a particular theory, this deformation and structure is thought to occur because as a substance crosses the boundary from liquid to gas, the substance volatilizes such that the volume of the liquid decreases. As this happens, surface tension at the solid-liquid interface pulls against any structures to which the liquid is attached. Delicate surface structures tend to be broken apart by this surface tension. Such damage may be caused by the effects of surface tension on the liquid/gas interface. Critical point drying is a technique that avoids effects of surface tension on the liquid/gas interface by substantially preventing a liquid/gas interface from developing. Critical point or supercritical drying does not cross any phase boundary, instead passing through the supercritical region, where the distinction between gas and liquid ceases to apply. As a result, materials dehydrated using critical point drying are not exposed to damaging surface tension forces. When the critical point of the liquid is reached, it is possible to pass from liquid to gas without abrupt change in state. Critical point drying can be used with bone matrices to phase change from liquid to dry gas without the effects of surface tension. Accordingly, bone dehydrated using critical point drying can retain or increase at least some of the surface structure and therefore the surface area.

In some embodiments, critical point drying is carried out using carbon dioxide. However, other mediums such as Freon, including Freon 13 (chlorotrifluoromethane), may be used. Generally, fluids suitable for supercritical drying include carbon dioxide (critical point 304.25 K at 7.39 MPa or 31.1° C. at 1072 psi or 31.2° C. and 73.8 bar) and Freon (about 300 K at 3.5-4 MPa or 25 to 30° C. at 500-600 psi). Nitrous oxide has similar physical behavior to carbon dioxide, but is a powerful oxidizer in its supercritical state. Supercritical water is also a powerful oxidizer, partly because its critical point occurs at such a high temperature (374° C.) and pressure (3212 psi/647K and 22.064 MPa).

In some embodiments, the bone may be pretreated to remove water prior to critical point drying. Thus, in accordance with one embodiment, bone matrix is dried using carbon dioxide in (or above) its critical point status. After demineralization, bone matrix samples (in water) may be dehydrated to remove residual water content. Such dehydration may be, for example, through a series of graded ethanol solutions (for example, 20%, 50%, 70%, 80%, 90%, 95%, 100% ethanol in deionized water). In some embodiments, penetrating the tissue with a graded series of ethanol solutions or alcohols may be accomplished in an automated fashion. For example, pressure and vacuum could be used to accelerate penetration into the tissue.

Methods of Use

A method of implanting a bone implant at a surgical site beneath the skin of a patient is provided. The bone implants implanted by this method can be the bone implants shown in FIGS. 1-9, and the surgical site of the method is a posterior lateral segment of the spine. The method can also be employed in a surgical treatment with a patient in a prone or supine position, and/or employ various surgical approaches to the spine, including anterior, posterior, posterior mid-line, direct lateral, and/or antero-lateral approaches, and in other body regions. The method may also be employed with procedures for treating the lumbar, cervical, thoracic, sacral and pelvic regions of a spinal column. The method may also be used on animals, bone models and other non-living substrates, such as, for example, in training, testing and demonstration.

In some embodiments, the method comprises delivering to the surgical site a plurality of bone fasteners, a spinal rod, and the bone implant, the bone implant comprising a mesh body having a distal end and a proximal end and a compartment disposed therebetween, the compartment configured to receive a bone material, a first cylindrical member disposed at or near the proximal end of the mesh body, the first cylindrical member configured for engagement with the spinal rod to facilitate containment of the bone material at the surgical site, and a second cylindrical member disposed at or near the distal end of the mesh body, the second cylindrical member configured for engagement with the spinal rod to facilitate containment of the bone material at the surgical site; attaching the plurality of bone fasteners to surgical site; attaching the first and second cylindrical members to the spinal rod; and attaching the spinal rod to the plurality of bone fasteners in a fixed engagement.

The first and second cylindrical members can be resorbable grommets that are configured for at least partial slidable engagement with the spinal rod, the mesh body is a net, and the bone material comprises fully demineralized bone fibers and surface demineralized bone chips.

In the above described method, the bone implant is delivered to the surgical site via a dilator system, as shown in FIGS. 1-3, the dilator system comprising a first sleeve having an interior surface that defines a channel; and a second sleeve having an outer surface, an inner surface and a distal end, the inner surface of the second sleeve defining an inner channel, the outer surface of the second sleeve configured to slidably engage the interior surface of the channel of the first sleeve, wherein the bone implant is disposed in a portion of the channel of the first sleeve or is disposed in a portion of the inner channel of the second sleeve, or is disposed in both the portion of the channel of the first sleeve and the portion of the inner channel of the second sleeve, such that sliding the outer surface of the second sleeve deploys the bone implant at the surgical site.

In some embodiments, a method of implanting a bone implant is provided, as shown in FIGS. 1-3, the method comprising positioning a first sleeve having an interior surface that defines a channel; positioning a second sleeve having an outer surface and an inner surface, the inner surface of the second sleeve defining an inner channel, the outer surface of the second sleeve configured to slidably engage the interior surface of the channel of the first sleeve; slidably engaging the second sleeve within the first sleeve; disposing a bone implant comprising a mesh material in a portion of the channel of the first sleeve, in a portion of the inner channel of the second sleeve, or in both the portion of the channel of the first sleeve and the portion of the inner channel of the second sleeve, such that sliding the outer surface of the second sleeve deploys and implants the bone implant at the surgical site.

In the above described method, the first sleeve and the second sleeve are dilators; the first sleeve has a diameter that is greater than a diameter of the second sleeve, and the bone implant has a diameter that is greater than the diameter of the second sleeve; or the bone implant further comprises a bone material.

In some embodiments, the bone implant may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others. The bone implant may be used in a minimally invasive procedure via placement through a small incision, via delivery through the dilators, or other means. The size and shape may be designed with restrictions on delivery conditions.

In some embodiments, the bone implant is flexible enough so that it can be folded upon itself before it is implanted at, near, or in the surgical site.

Generally, the bone implant may be applied to a pre-existing defect, to a created channel, or to a modified defect. Thus, for example, a channel may be formed in a bone, or a pre-existing defect may be cut to form a channel, for receipt of the bone implant. The bone implant may be configured to match the channel or defect. In some embodiments, the configuration of bone implant may be chosen to match the channel. In other embodiments, the channel may be created, or the defect expanded or altered, to reflect a configuration of the bone implant. The bone implant may be placed in the defect or channel and, optionally, coupled using attachment mechanisms.

Although the invention has been described with reference to embodiments, persons skilled in the art will recognize that changes may be made in form and detail without departing from the spirit and scope of the invention

What is claimed is:

1. A kit for deploying a bone implant at a surgical site, the kit comprising:
    a first sleeve having an interior surface that defines a channel, the first sleeve having a tapered distal end tapering toward a central axis of the first sleeve;
    a second sleeve having an outer surface and an inner surface, the inner surface of the second sleeve defining an inner channel, the outer surface of the second sleeve configured to slidably engage the interior surface of the channel of the first sleeve, the second sleeve also having a tapered distal end tapering toward a central axis of the first sleeve, the distal end including a capturing mechanism configured to fasten to the bone implant such that the second sleeve engages the bone implant such that the tapered distal end is configured to deploy the bone implant directly to the surgical site; and
    the bone implant comprises a mesh material partially enclosing a bone material before the bone implant deploys, the mesh material disposed in a portion of the channel of the first sleeve or disposed in a portion of the inner channel of the second sleeve or disposed in both the portion of the channel of the first sleeve and the portion of the inner channel of the second sleeve such that sliding the outer surface of the second sleeve deploys the bone implant at the surgical site, the mesh being configured to be held and compressed inside the first sleeve and the mesh comprising an attachment mechanism comprising a grommet allowing a screw to affix the mesh at the surgical site so that the bone material does not migrate away from the surgical site after the mesh is deployed away from the first sleeve and the second sleeve, wherein the mesh is attached to the outer surface at the distal end of the second sleeve and the mesh is perpendicular to a longitudinal axis of the second sleeve with the capturing mechanism comprising hooks, anchors, buttons, clips, snaps, friction fittings, compressive fittings, expanding rivets, staples, nails, posts, connectors, or a combination thereof, the capture mechanism located at the distal end of the second sleeve.

2. The kit according to claim 1, wherein the first sleeve and the second sleeve are dilators; and the first sleeve has a diameter that is greater than a diameter of the second sleeve, and the bone implant has a diameter that is greater than the diameter of the second sleeve.

3. The kit according to claim 1, wherein the second sleeve comprises an engagement member disposed on the outer surface of the second sleeve and is configured for engagement with the channel of the first sleeve.

4. The kit according to claim 3, wherein the engagement member is made from one or more metals, plastics, polymers, or a combination thereof.

5. The kit according to claim 1, wherein the mesh material is made from resorbable natural or synthetic polymers comprising at least one of poly(lactic acid) (PLA), poly (glycolic acid) (PGA), poly(lactic-co-glycolic acid) (PLGA), silk, or a combination thereof.

6. The kit according to claim 1, wherein the kit further comprises fastening elements comprising resorbable screws, resorbable tacks, adhesives, or a combination thereof.

* * * * *